United States Patent
Ben-Haim

(10) Patent No.: US 12,245,939 B2
(45) Date of Patent: Mar. 11, 2025

(54) METHODS AND DEVICES FOR DEPLOYMENT OF A TRANSCATHETER HEART VALVE

(71) Applicant: Libra Science Ltd., Tortola (VG)

(72) Inventor: Shlomo Ben-Haim, Châtelaine (CH)

(73) Assignee: Libra Science Ltd., Road Town (VG)

( * ) Notice: Subject to any disclaimer, the term of this patent is extended or adjusted under 35 U.S.C. 154(b) by 0 days.

(21) Appl. No.: 18/429,549

(22) Filed: Feb. 1, 2024

(65) Prior Publication Data
US 2024/0261094 A1 Aug. 8, 2024

Related U.S. Application Data

(60) Provisional application No. 63/442,779, filed on Feb. 2, 2023.

(51) Int. Cl.
| | | |
|---|---|---|
| A61F 2/24 | (2006.01) | |
| A61B 17/02 | (2006.01) | |
| A61M 25/09 | (2006.01) | |
| A61M 25/10 | (2013.01) | |

(52) U.S. Cl.
CPC ........ *A61F 2/2436* (2013.01); *A61B 17/0218* (2013.01); *A61M 25/09* (2013.01); *A61M 25/10* (2013.01)

(58) Field of Classification Search
CPC .. A61F 2/2436; A61B 17/0218; A61M 25/09; A61M 25/10
See application file for complete search history.

(56) References Cited

U.S. PATENT DOCUMENTS

| | | | |
|---|---|---|---|
| 2005/0137696 A1* | 6/2005 | Salahieh | A61F 2/2439 623/2.11 |
| 2011/0098804 A1* | 4/2011 | Yeung | A61F 2/2412 623/2.1 |
| 2012/0016342 A1* | 1/2012 | Brecker | A61M 25/09 604/528 |
| 2013/0035759 A1* | 2/2013 | Gross | A61F 2/246 623/2.38 |
| 2016/0220369 A1* | 8/2016 | Chalekian | A61F 2/2436 |
| 2018/0116678 A1* | 5/2018 | Melanson | A61B 17/12131 |
| 2018/0344454 A1* | 12/2018 | Mauch | A61F 2/844 |

(Continued)

OTHER PUBLICATIONS

Webb, John; et. al. "Transcatheter Valve-in-Valve Implantation for Failed Bioprosthetic Heart Valves." Circulation, vol. 121, No. 16, Apr. 27, 2010, pp. 1848-1857. https://www.ahajournals.org/doi/10.1161/CIRCULATIONAHA.109.924613 (Year: 2010).*

(Continued)

*Primary Examiner* — Sarah W Aleman
*Assistant Examiner* — Rachel S Highland

(57) ABSTRACT

There is provided a method of treating a patient, comprising: delivering a self-expandable transcatheter heart valve (THV) over a guidewire in a contracted state and within a sheath to a first anatomical location within a heart of the patient, moving the THV relative to the sheath for partially self-expanding a portion of the THV within the first anatomical location, wherein a portion of the THV in the sheath remains in the contracted state and the THV is partially self-expanded, and refraining from moving the partially self-expanded THV, relative to the aortic annulus of the heart.

29 Claims, 9 Drawing Sheets

(56) References Cited

U.S. PATENT DOCUMENTS

2019/0201191 A1* 7/2019 McLean ............... A61F 2/246
2023/0009249 A1* 1/2023 Cohen ................. A61F 2/2418

OTHER PUBLICATIONS

Abbott "Portico™ Transcatheter Aortic Valve Implantation System: Portico™ Transcatheter Aortic Valve, FlexNav™ Delivery System, FlexNav™ Loading System", Abbott, Instruction for Use, Ref. PRT-23, PRT-25, PRT-27, PRT-29 FNAV-DS-SM, FNAV-DS-LG FNAV-LS-SM, FNAV-LS-LG, p. 1-44, Jun. 2020.
Boston Scientific "ACURATE Neo Transfemoral Delivery System—Specifications", Boston Scientific, Product Overview, 2 P., 2019.
Boston Scientific Corporation "ACURATE Neo™ Transfemoral Delivery System", Boston Scientific, p. 1-48, May 2018.
Edwards Lifesciences "Edwards SAPIEN 3 Kit—Transfemoral", Edwards Lifesciences, Instructions for Use, p. 1-9, Nov. 2016.
Edwards Lifesciences "Edwards SAPIEN 3: Transcatheter Heart Valve With the Edwards Commander Delivery System", Edwards Lifesciences, Instruction for Use, p. 1-30, 2015.
Medtronic "CoreValve™ Evolut™ R System: CoreValve™ Evolut™ R Transcatheter Aortic Valve, Delivery Catheter System, Loading System", Medtronic, M056197T001 Rev. AA, M970312A001 Rev. AA, p. 1-209, 2019.

* cited by examiner

METHODS AND DEVICES FOR DEPLOYMENT OF A TRANSCATHETER HEART VALVE

RELATED APPLICATION(S)

This application claims the benefit of priority of U.S. Provisional Patent Application No. 63/442,779 filed on Feb. 2, 2023, the contents of which are incorporated herein by reference in their entirety.

FIELD AND BACKGROUND OF THE INVENTION

The present invention, in some embodiments thereof, relates to medical treatment methods and/or medical devices and, more particularly, but not exclusively, to transcatheter valve replacement procedures.

In contrast to standard surgical replacement of a heart valve, which involves open heart surgery, transcatheter valve replacement procedures deliver artificial heart valves to the heart via a small incision to an artery (usually the femoral artery) threading the heart valve via arteries to the heart, and expanding the artificial valve within the heart for deploying the artificial valve within the heart.

SUMMARY OF THE INVENTION

According to a first aspect, a method of treating a patient, comprises: delivering a self-expandable transcatheter heart valve (THV) over a guidewire in a contracted state and within a sheath to a first anatomical location within a heart of the patient, moving the THV relative to the sheath for partially self-expanding a portion of the THV within the first anatomical location, wherein a portion of the THV in the sheath remains in the contracted state and the THV is partially self-expanded, and refraining from moving the partially self-expanded THV, relative to an aortic annulus of the heart.

According to a second aspect, a method of treating a patient, comprises: delivering a self-expandable transcatheter heart valve (THV) over a guidewire and within a sheath to a first anatomical location within a heart of the patient, moving the THV relative to the sheath for partially self-expanding a portion of the THV within the first anatomical location, wherein a portion of the THV in the sheath remains in a contracted state, completing the withdrawal of the sheath for expanding the portion of the THV in the contracted state while refraining from moving the THV, relative to an aortic annulus of the heart.

According to a third aspect, a method of treating a patient, comprises: delivering a self-expandable transcatheter heart valve (THV) in a contracted state over a guidewire and within a sheath to a first anatomical location within a heart of the patient, moving the THV relative to the sheath for partially self-expanding a portion of the THV within the first anatomical location, wherein a portion of the THV in the sheath remains in the contracted state, and re-compressing the expanded portion of the THV by moving the sheath over the expanded portion of the THV while refraining from moving the THV relative to an aortic annulus of the heart and positioning the compressed THV to a second anatomical location.

According to a fourth aspect, a method of treating a patient, comprises: delivering a self-expandable transcatheter heart valve (THV) over a guidewire in a contracted state and within a sheath to a first anatomical location within a heart of the patient, moving the THV relative to the sheath for partially self-expanding a portion of the THV within the first anatomical location, wherein a portion of the THV in the sheath remains in the contracted state and the THV is partially self-expanded, without moving the partially self-expanded portion of the THV within the heart, distally displacing the sheath relative to the partially self-expanded portion of the THV for re-collapsing the partially self-expanded portion of the THV into the contracted state, after the re-collapsing of the partially self-expanded portion, repositioning the THV to a second anatomical location within the heart, and moving the THV relative to the sheath for full self-expansion of the THV within the second anatomical location.

According to the fourth aspect, the second anatomical location is within a previously implanted artificial heart valve that has malfunctioned.

In a further implementation form of the first, second, third, and fourth aspects, refraining from moving the partially self-expanded portion of the THV within the heart is selected from a group comprising: not proximally displacing, not distally displacing, and not rotating.

In a further implementation form of the first, second, third, and fourth aspects, first anatomical location excludes a target anatomical location for implantation of the THV.

In a further implementation form of the first, second, third, and fourth aspects, the first anatomical location within the heart includes a conduction system of the heart, and movement of the portion of the THV that is expanded within the first anatomical location is likely to damage the conduction system, and further comprising re-collapsing the partially self-expanded portion, and repositioning the THV after the re-collapsing, for avoiding or reducing damage to the conduction system from movement of the portion of the THV that is expanded within the first anatomical location.

In a further implementation form of the first, second, third, and fourth aspects, the portion of the THV is partially self-expanded when a distal end of the THV is larger by at least about 3 millimeters above a diameter of the THV in the contracted state.

In a further implementation form of the first, second, third, and fourth aspects, further comprising starting release of a nose element of the THV after a distal end of a nose element of a delivery system of the THV passed through the aortic annulus.

In a further implementation form of the first, second, third, and fourth aspects, further comprising inflating a balloon within a native valve in which the self-expandable THV is to deployed prior to passing the self-expandable THV over the guidewire.

In a further implementation form of the first, second, third, and fourth aspects, further comprising prior to inflating the balloon, checking whether a second catheter is positioned in proximity to the aortic annulus, and not inflating the balloon when the second catheter is positioned in proximity to the aortic annulus.

In a further implementation form of the first, second, third, and fourth aspects, the second catheter is positioned in proximity to the aortic annulus comprises the second catheter is positioned within about 4 centimeters (cm) from the aortic annulus.

In a further implementation form of the first, second, third, and fourth aspects, the second catheter is positioned in proximity to the aortic annulus comprises the second catheter is positioned between aortic valve cusps of the aortic valve.

In a further implementation form of the first, second, third, and fourth aspects, further comprising prior to the inflating the balloon, moving the second catheter from tissues being compressed by expansion of the balloon during inflation.

In a further implementation form of the first, second, third, and fourth aspects, further comprising prior to inflating the balloon, moving the second catheter to a left coronary cusp.

In a further implementation form of the first, second, third, and fourth aspects, further comprising inflating the balloon while maintaining a constant location of the balloon during inflation from an initial position of the balloon at the beginning of inflation.

In a further implementation form of the first, second, third, and fourth aspects, further comprising prior to delivering the THV over the guidewire, inserting the guidewire used for delivering the THV into the left ventricle.

In a further implementation form of the first, second, third, and fourth aspects, further comprising during the insertion of the guidewire, creating curves of the guidewire each of a local radius of at least about 0.6 millimeters (mm), wherein no curve of the guidewire is less than about 0.6 mm.

In a further implementation form of the first, second, third, and fourth aspects, further comprising maintaining a substantially constant location of a distal end of the guidewire while at least one of the THV and a balloon are being delivered over the guidewire and/or removed over the guidewire.

In a further implementation form of the first, second, third, and fourth aspects, the distal end of the guidewire is maintained in the substantially constant location within the left ventricle.

In a further implementation form of the first, second, third, and fourth aspects, the patient suffers from a non-healthy aortic heart valve, and the patient is treated using a transcatheter aortic valve replacement (TAVR) procedure for replacing the non-healthy aortic heart valve with a transcatheter aortic valve.

In a further implementation form of the first, second, third, and fourth aspects, the patient suffers from aortic stenosis.

In a further implementation form of the first, second, third, and fourth aspects, further comprising moving the THV relative to the sheath for full self-expansion of the THV within a second anatomical location within the heart.

According to a fifth aspect, a delivery system for delivery of a self-expandable transcatheter heart valve (THV) to an anatomical location within a heart of a patient, comprises: an expansion controller for controlling expansion and re-collapse of the self-expandable THV, comprising a mechanism for changing an operator applied rate of axial distal displacement or proximal displacement of a capsule housing the self-expandable THV for expanding or re-collapse of the self-expandable THV, to another rate of axial distal displacement or proximal displacement of the capsule for expanding or re-collapse of the self-expandable THV that is different than the operator applied rate.

In a further implementation form of the fifth aspect, further comprising a shaft assembly including a shaft for delivery of the THV, the shaft assembly including the capsule and a nose element shaped as a cone located at a distal end of the shaft in proximity to the capsule, the cone having a length of less than about 6 mm.

In a further implementation form of the fifth aspect, further comprising a shaft assembly including a shaft for delivery of the THV, the shaft assembly including a capsule for housing the THV and a nose element shaped as a rounded dome located at a distal end of the shaft in proximity to the capsule.

In a further implementation form of the fifth aspect, a length of the rounded dome is less than about 4 mm.

In a further implementation form of the fifth aspect, a radius and a shape of the rounded dome substantially matches an inner radius and shape of the capsule.

In a further implementation form of the fifth aspect, the expansion controller includes a selector for selecting between one of the axial distal displacement or the proximal displacement of the capsule.

In a further implementation form of the fifth aspect, the expansion controller changes the operator applied rate to another rate that is pre-set to provide a fast deployment within a preselected amount of time to a preselected percentage of a total radius of a fully self-expanded TVH.

In a further implementation form of the fifth aspect, the expansion controller includes a stepper mechanism that includes a plurality of steps that distally displaces the capsule or proximally displaces the capsule a predefined length for each step.

In a further implementation form of the fifth aspect, the expansion controller is configured to provide a different ratio between a rate of proximal displacement for covering the capsule and a rate of distal displacement for uncovering the capsule.

In a further implementation form of the fifth aspect, the rate of proximal displacement is greater than the rate of proximal displacement for a same movement of the expansion controller.

In a further implementation form of the fifth aspect, further comprising a shaft assembly including a shaft for delivery of the THV, the shaft assembly including a capsule for housing the THV and a nose element located at a distal end of the shaft in proximity to the capsule, wherein at least one of the capsule and the nose element include an inner channel designed to accommodate a guidewire threaded therethrough, wherein at least one of the capsule and the nose element are designed for adjustment of pose of a distal portion of the nose element relative to the capsule, and the nose element includes an eccentrically shaped aperture through which the guidewire passes.

In a further implementation form of the fifth aspect, further comprising: a shaft assembly including a shaft for delivery of the THV, the shaft assembly including a capsule for housing the THV and a nose element located at a distal end of the shaft in proximity to the capsule, and a nose release mechanism designed for quick release of the nose element from the shaft assembly.

According to a sixth aspect, a method of treating a patient, comprises: delivering a self-expandable transcatheter heart valve (THV) over a guidewire and within a sheath to a first anatomical location within the heart, moving the THV relative to the sheath for partially self-expanding a portion of the THV within the first anatomical location, wherein a portion of the THV in the sheath remains in a contracted state, wherein the portion of the THV is partially self-expanded when a distal end of the THV is larger by at least about 3 millimeters above a diameter of the THV in the contracted state, and moving the THV relative to the sheath for full self-expansion of the THV within a second anatomical location within the heart.

According to a seventh aspect, a method of treating a patient, comprises: delivering a self-expandable transcatheter heart valve (THV) over a guidewire and within a sheath to a first anatomical location within the heart, not moving the THV relative to the sheath for partially self-expanding a portion of the THV, wherein a portion of the THV in the sheath remains in a contracted state, wherein the portion of the THV is partially self-expanded when a distal end of the THV is larger by at least about 3 millimeters above a diameter of the THV in the contracted state, and moving the THV relative to the sheath for full self-expansion of the THV for implantation.

According to an eighth aspect, a delivery system for delivery of a self-expandable transcatheter heart valve (THV) to an anatomical location within a heart of a patient, comprises: a shaft assembly including a shaft sized and shaped for delivery of the THV, the shaft assembly including a capsule and a nose element, the capsule sized and shaped for housing the self-expandable THV in a contracted state, and the nose element sized and shaped as a cone located at a distal end of the shaft in proximity to the capsule, the cone having a length of less than about 6 mm.

According to a ninth aspect, a delivery system for delivery of a self-expandable transcatheter heart valve (THV) to an anatomical location within a heart of a patient, comprises: a shaft assembly including a shaft sized and shaped for delivery of the THV, the shaft assembly including a capsule and a nose element, the capsule sized and shaped for housing the self-expandable THV in a contracted state, and the nose element sized and shaped as a rounded dome located at a distal end of the shaft in proximity to the capsule, wherein a length of the rounded dome is less than about 4 mm, and a radius and a shape of the rounded dome substantially matches an inner radius and shape of the capsule.

According to a tenth aspect, a delivery system for delivery of a self-expandable transcatheter heart valve (THV) to an anatomical location within a heart of a patient, comprises: a shaft assembly including a shaft sized and shaped for delivery of the THV, the shaft assembly including a capsule and a nose element, wherein at least one of the capsule and the nose element include an inner channel designed to accommodate a guidewire threaded therethrough, wherein at least one of the capsule and the nose element are designed for adjustment of pose of a distal portion of the nose element relative to the capsule, and the nose element including an eccentrically shaped aperture through which the guidewire passes.

According to an eleventh fifth aspect, a delivery system for delivery of a self-expandable transcatheter heart valve (THV) to an anatomical location within a heart of a patient, comprises: a shaft assembly including a shaft sized and shaped for delivery of the THV, the shaft assembly including a capsule and a nose element, and a nose release mechanism designed for quick release of the nose element from the shaft assembly.

According to a twelfth aspect, a method of treating a patient comprises: in response to deploying a transcatheter heart valve (THV) in a target anatomical location of a heart of the patient using a catheter of a delivery system, exchanging a stiff guidewire over which the catheter is riding to a soft guidewire, and extracting the delivery system from the body of the patient over the soft guidewire.

In a further implementation form of the twelfth aspect, the target anatomical location comprises an aortic valve annulus, and a distal region of the stiff guidewire is located in the left ventricle, wherein exchanging comprises placing a distal region of the soft guidewire in the left ventricle, wherein the delivery system is extracted while retaining the distal region of the soft guidewire in the left ventricle.

In a further implementation form of the twelfth aspect, further comprising prior to exchanging the stiff guidewire, retracting the catheter proximally to the deployed THV until a distal end of the catheter is located proximally to the deployed THV, and performing the exchanging while the distal end of the catheter is located proximally to the deployed THV by inserting a distal end of the soft guidewire though the deployed THV into a left ventricle.

In a further implementation form of the twelfth aspect, further comprising prior to exchanging the stiff guidewire, distally displacing a distal end of the catheter into a left ventricle by crossing the deployed THV, and performing the exchanging while the distal end of the catheter is located within the left ventricle and crossing the THV by inserting a distal end of the soft guidewire though the distal end of the catheter into the left ventricle.

In a further implementation form of the twelfth aspect, further comprising extracting the soft guidewire out of the body of the patient after extracting the delivery system out of the body of the patient.

In a further implementation form of the twelfth aspect, the stiff guidewire is exchanged without positioning the distal region of the catheter and a distal region of the stiff guidewire in a substantially center of the deployed THV.

In a further implementation form of the twelfth aspect, the stiff guidewire is capable of crossing a stenotic native aortic valve to be replaced with the THV, and the soft guidewire bends in response to an attempt to cross the stenotic native aortic valve without crossing the stenotic native aortic valve.

In a further implementation form of the twelfth aspect, the stiff guidewire is capable of damaging tissue of the interior of the heart by distal displacement into the tissue, and the soft guidewire bends in response to distal displacement into the tissue and does not cause the damage to the tissue that is caused by the stiff guidewire.

According to a thirteenth aspect, a method of treating a patient comprises: implanting a transcatheter heart valve (THV) in an aortic annulus of an aortic valve of the patient by positioning a distal end of the THV about 3-10 mm from a plane defined as a bottom of cusps of the aortic valve in a direction towards a left ventricle.

In a further implementation form of the thirteenth aspect, the THV comprises a first THV, wherein the first THV is implanted at a location within the aortic annulus selected to enable deployment of a second THV within the first deployed THV without dislodging the first THV from the location.

According to a fourteenth aspect, a method of treating a patient, comprises: delivering a balloon to an interior of a heart valve of the patient, maintaining a constant location of the balloon within the heart valve during inflation of the balloon and maintain the constant location while the balloon is inflated.

In a further implementation form of the fourteenth aspect, maintaining the constant location of the balloon comprises not proximally displacing or distally displacing the balloon.

In a further implementation form of the fourteenth aspect, the balloon is inflated within an aortic valve prior to implanting of a transcatheter heart valve (THV) in the aortic valve.

In a further implementation form of the fourteenth aspect, the balloon is inflated after implantation of the THV.

In a further implementation form of the fourteenth aspect, the balloon is inflated in a previously implanted THV.

According to a fifteenth aspect, a method of treating a patient, comprises: passing a transcatheter heart valve (THV) through an annulus of an aortic valve, the THV delivered within a capsule connected to a nose element, and after passing the annulus and before the nose element contacts inner tissue of the heart, releasing the nose element from the capsule such that the released nose element is configured for freely swiveling.

In a further implementation form of the fifteenth aspect, the nose element is released when the nose element is at the level of a plane defining the aortic annulus.

According to a sixteenth aspect, a method of treating a patient, comprises: prior to passing a device into and/or past an aortic valve, proximally retracting a catheter from a left ventricle and past the aortic valve, and in response to the catheter's retraction, passing the device into and/or past the aortic valve.

In a further implementation form of the sixteenth aspect, the catheter is retracted from cusps of the aortic valve.

In a further implementation form of the sixteenth aspect, the device is selected from a group comprising: a transcatheter heart valve (THV) for implantation in the aortic valve, and a balloon for inflation in the aortic valve.

In a further implementation form of the sixteenth aspect, the catheter is proximally retracted prior to inflation of the balloon within the aortic valve.

According to a seventeenth aspect, a method of treating a patient comprises: monitoring a guidewire placed within an organ of a patient for detecting a curvature of the guidewire less than a threshold, and manipulating the guidewire for increasing the curvature above the threshold.

In a further implementation form of the seventeenth aspect, the threshold indicates risk of damage to tissue to pressure applied at a region of the guidewire having the curvature.

In a further implementation form of the seventeenth aspect, the threshold is about 0.6 mm.

In a further implementation form of the seventeenth aspect, the guidewire is a stiff guidewire.

In a further implementation form of the seventeenth aspect, the guidewire is passed across an annulus of an aortic valve, and a distal end of the guidewire is located within a left ventricle of a heart.

In a further implementation form of the seventeenth aspect, the method is used in a transcatheter aortic valve replacement (TAVR) procedure.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings and/or images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 5A:
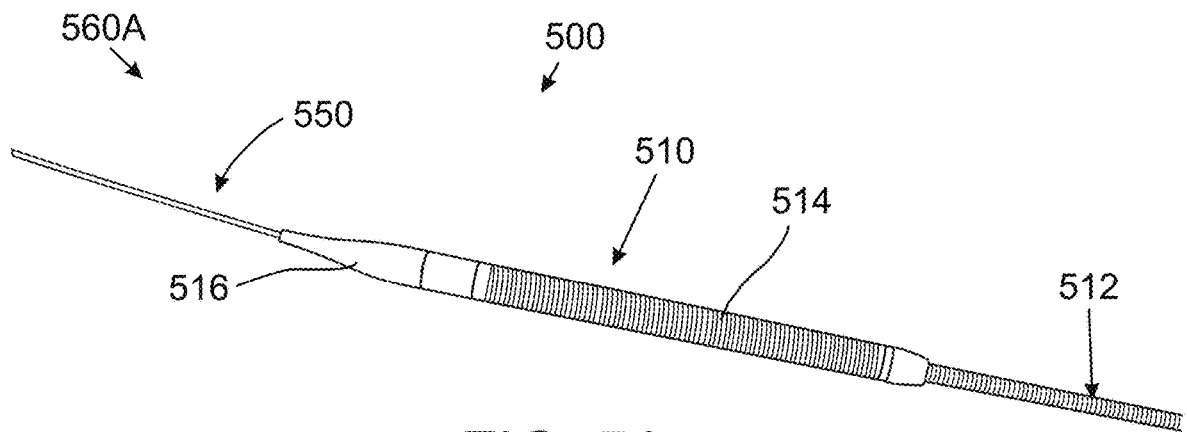
Figure 5B:
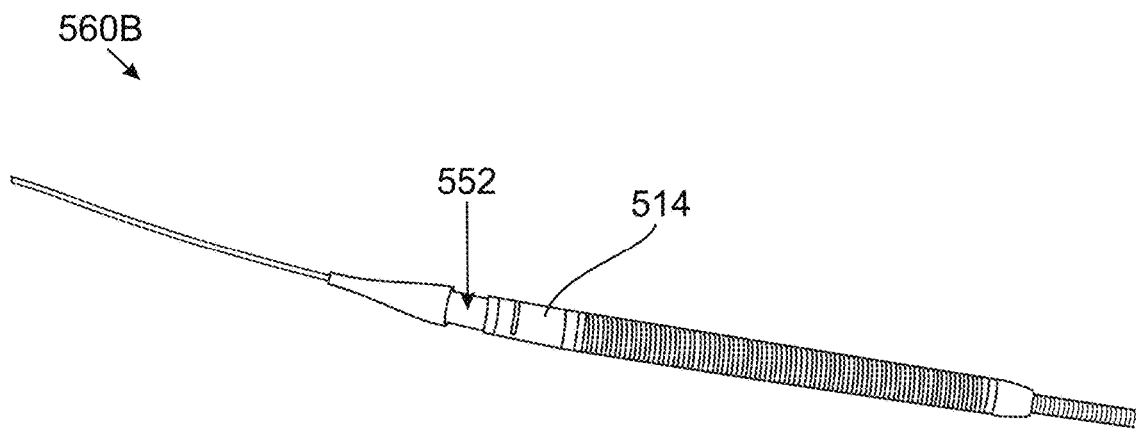
Figure 5C:
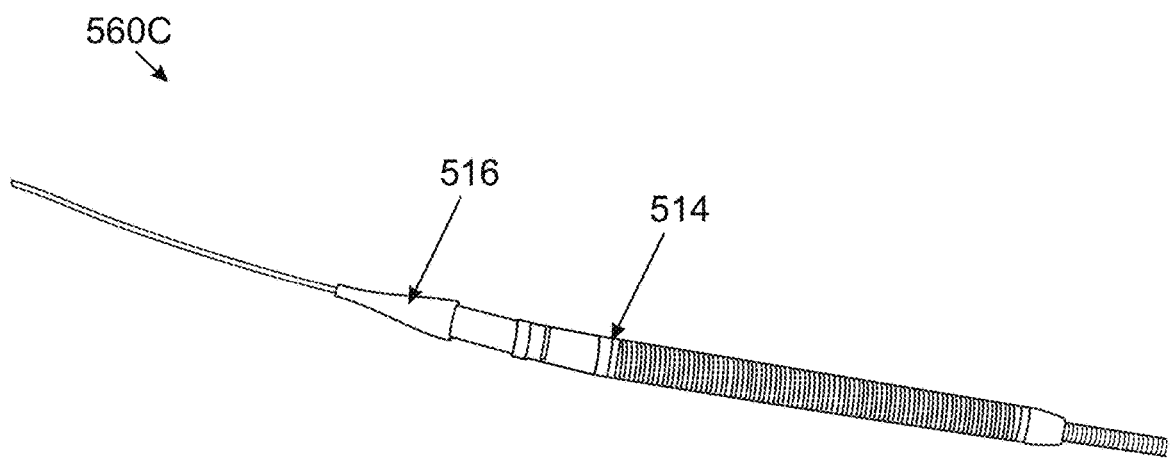
Figure 5D:
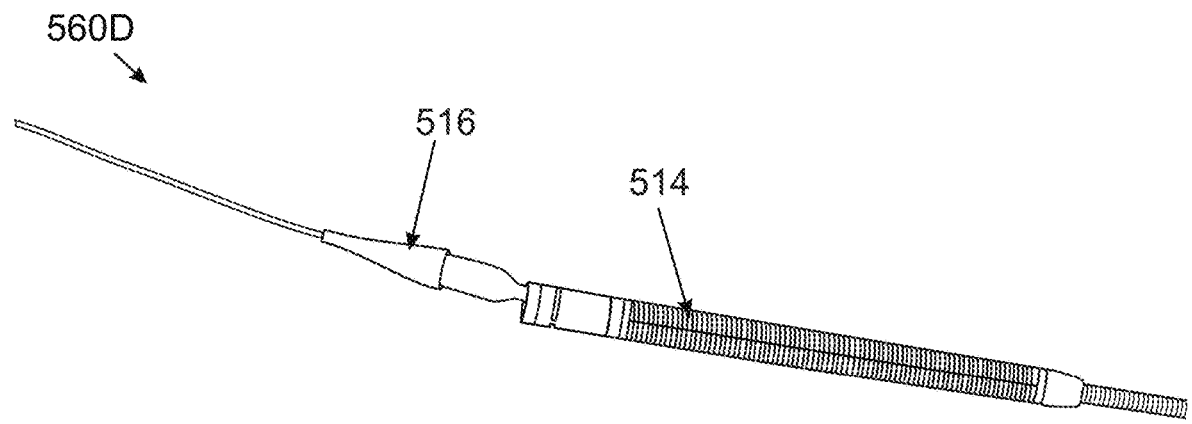
Figure 5E:
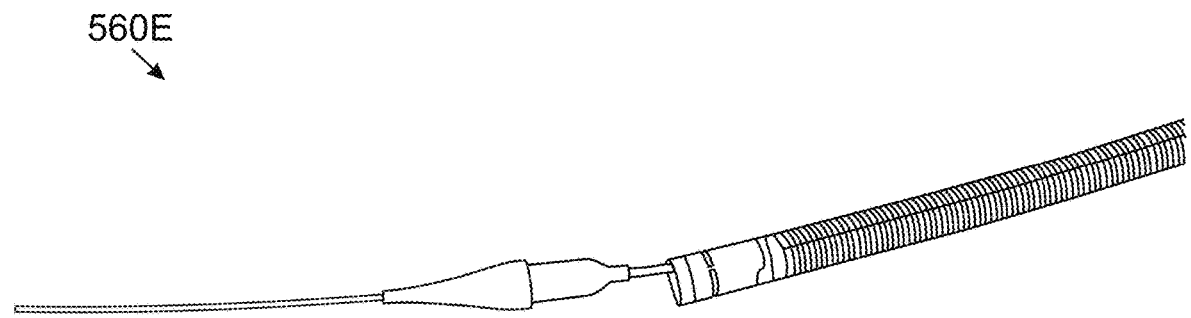
Figure 6:
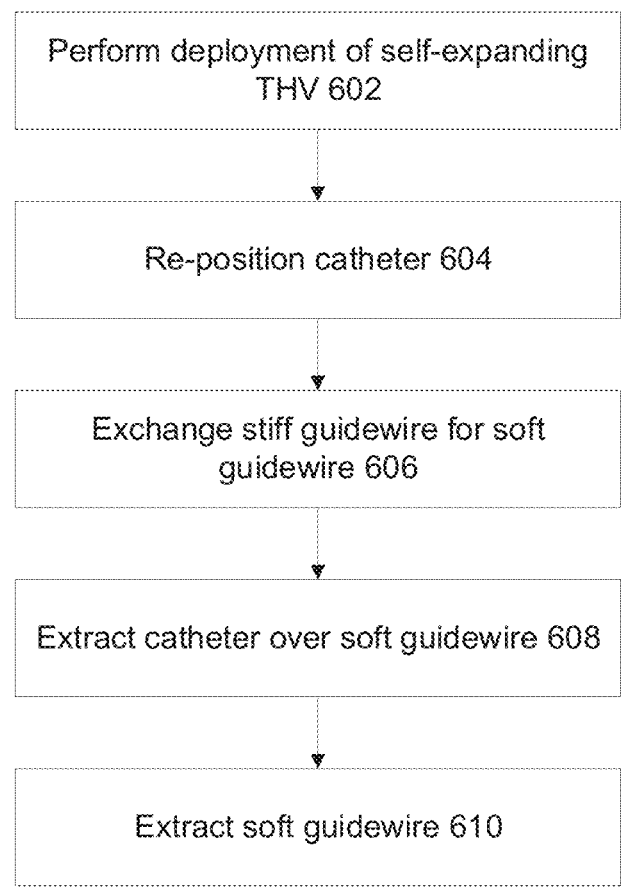

FIGS. 5A-5E include schematics of separating a nose element from a capsule passed over a guidewire, in accordance with some embodiments of the present invention; and FIG. 6 is a method of exchanging a stiff guidewire with a soft guidewire, in accordance with some embodiments of the present invention.

DESCRIPTION OF SPECIFIC EMBODIMENTS OF THE INVENTION

The present invention, in some embodiments thereof, relates to medical treatment methods and/or medical devices and, more particularly, but not exclusively, to transcatheter valve replacement procedures.

As used herein, the term distal and proximal are with reference to an operator located outside of the body of the subject in which the transcatheter heart valve is being implanted. Distal may refer to displacement and/or advancement of devices (e.g., guidewire, delivery system, transcatheter heart valve) deeper into the body of the subject and/or away from the operator. Proximal may refer to retraction and/or withdrawing of device out of the body of the subject and/or towards the operator. With reference to the aortic valve (e.g., for aortic valve replacement), the term distal may refer to movement in the retrograde direction, and the term proximal may refer to movement in the antegrade direction.

As used herein, the term sheath may sometimes be interchanged with the term capsule and/or catheter, for example, the THV may be delivered to the anatomical location within a sheath and/or within a capsule and/or within a catheter. In another example, the sheath and/or the capsule and/or catheter may be retracted for expansion of THV, as described herein. In yet another example, the capsule which includes the THV may be delivered within the sheath. In yet another example, the catheter includes the sheath and the capsule.

As used herein, the term aortic annulus may refer to different locations as commonly used, for example, by different physicians and/or different clinical guidelines. The definition of the aortic annulus as a plane of the bottom of cusps of the aortic valve (i.e., towards the left ventricle) is one example, and is not necessarily meant to be limiting. Other definitions of the aortic annulus can be used, for example, a higher line towards the left atrium.

As used herein, the terms sheath, catheter, and delivery system may sometimes be interchanged. The terms sheath, catheter, and delivery system may refer to the device used to deliver the THV into the anatomical location within the heart (e.g., to the aortic annulus and/or previously deployed THV).

Some embodiments described herein that describe self-expansion of a self-expanded THV are to be understood as a not necessarily limiting example. It is to be understood that non-self-expanding THVs, for example, balloon expandable, THVs may be used. Some embodiments described with reference to self-expanding THVs may be modified to be apply to balloon expandable THVs (or other non-self-expanding approaches).

An aspect of some embodiments of the present invention relates to a method of treating a patient by delivering an expandable transcatheter heart valve (THV) into a heart, where throughout the procedure, when a portion of the THV is at least partially expanded within the heart (e.g., within the aortic annulus), the partially expanded portion of the THV is not moved within the heart, optionally not moved relative to the valve being replaced (e.g., aortic valve) and/or not moved relative to the aortic annulus, for example, not proximally displaced (e.g., antegrade), not distally displaced (e.g., retrograde), and/or not rotated. In order to move the at least partially expanded THV, the THV is retracted back into a fully contracted state. The contracted THV may be moved. Avoiding moving the THV in at least a partially expanded state, in which at least a portion of the THV has been expanded may reduce risk of damage to internal tissues of a heart (e.g., conduction system) in comparison to standard approaches of delivering the THV.

The THV may be, for example, self-expanded, and/or balloon expanded.

The method of treatment includes delivering the THV is within the contracted state over a guidewire and within a sheath (e.g., capsule and/or catheter) to a first anatomical location within the heart. The THV may be moved relative to the sheath (e.g., by proximally retracting the sheath, and/or by distally displacing the THV) for partially expanding a portion the THV within the first anatomical location. Another portion of the THV in the sheath may remain in the contracted state. It may be determined that the first anatomical location is different than a target anatomical location where the THV is to be implanted, in which case, the THV is to be moved to the target anatomical location. The expanded portion of the THV is not moved within the heart, for example, not proximally displaced (e.g., antegrade), not distally displaced (e.g., retrograde), and/or not rotated. In order to enable moving the THV to another location, the sheath is distally displaced relative to the partially expanded portion of the THV for re-collapsing the partially expanded portion of the THV into the contracted state. The re-collapsing of the partially expanded portion of the THV is done without moving the partially expanded portion of the THV relative to the heart. After the re-collapsing of the partially expanded portion, the THV may be re-positioned to a second anatomical location within the heart, which may be selected as the most likely location of the target anatomical location for deployment of the THV. The THV is moved relative to the sheath for full expansion of the THV within the second anatomical location (e.g., by proximally retracting the sheath, and/or by distally displacing the THV). Throughout the procedure, the expanded portion of THV is not moved within the heart and/or relative to the aortic valve.

As used herein, the phrase "not moved" (within the heart) may be interchanged with the phrase "maintaining a constant position and/or orientation". The constant location may be maintained by not proximally displacing and/or distally displacing and/or not rotating (e.g., the device, the THV, and/or the balloon).

An aspect of some embodiments of the present invention relates to a method of treating a patient by delivering a self-expandable transcatheter heart valve (THV) over a guidewire and within a sheath to a first anatomical location within the heart. The method includes moving the THV relative to the sheath for partially self-expanding a portion of the THV within the first anatomical location. A portion of the THV in the sheath remains in a contracted state. The method includes refraining from moving the partially expanded THV, relative to the aortic annulus.

An aspect of some embodiments of the present invention relates to a method of treating a patient by delivering a self-expandable THV over a guidewire and within a sheath to a first anatomical location within the heart. The method includes moving the THV relative to the sheath for partially self-expanding a portion of the THV within the first anatomical location. A portion of the THV in the sheath remains in a contracted state. The method includes completing the withdrawal of the sheath for expanding the rest of the compressed THV while refraining from moving the THV, relative to the aortic annulus.

An aspect of some embodiments of the present invention relates to a method of treating a patient by delivering a self-expandable THV over a guidewire and within a sheath to a first anatomical location within the heart. The method includes moving the THV relative to the sheath for partially self-expanding a portion of the THV within the first anatomical location. A portion of the THV in the sheath remains in a contracted state. The method includes re-compressing the expanded part of the THV by moving the sheath over the expanded portion of the THV while refraining from moving the THV, relative to the aortic annulus. The method includes positioning the closed (compressed) THV to a second anatomical location.

Another aspect of some embodiments of the present invention relates to a method of treating the patient by delivering a self-expandable transcatheter heart valve (THV) into the heart. The delivery of the THV may be done with reduced risk of damage to internal tissues of a heart (e.g., conduction system) in comparison to standard approaches of delivering the THV. The THV is delivered over a guidewire and within a sheath to a first anatomical location within the heart. The first anatomical location is different than the target anatomical location for deployment of the THV. The THV may be moved relative to the sheath for partially self-expanding a portion the THV within the first anatomical location, where a portion of the THV in the sheath remains in a contracted state. The portion of the THV is partially self-expanded when a distal end region of the THV is larger by at least about 3 millimeters (mm) (or 5 mm, or 7 mm or other intermediate or larger values) above a diameter of the THV in the contracted state. The THV may be moved relative to the sheath for full self-expansion of the THV within a second anatomical location within the heart. The second anatomical location may be the target anatomical location for deployment of the THV. Throughout the procedure, the self-expanded portion of THV is not moved within the heart and/or relative to the aortic valve.

Another aspect of some embodiments of the present invention relates to a method of treating the patient by delivering a self-expandable transcatheter heart valve (THV) into the heart. The delivery of the THV may be done with reduced risk of damage to internal tissues of a heart (e.g., conduction system) in comparison to standard approaches of delivering the THV. The THV may be delivered over a guidewire and within a sheath to a first anatomical location within the heart. The THV is not moved relative to the sheath for partially self-expanding a portion the THV. Throughout the procedure, the self-expanded portion of THV is not moved within the heart and/or relative to the aortic valve. The sheath may be moved relative to the THV, optionally by proximal retraction of the sheath. A portion of the THV in the sheath remains in a contracted state. The portion of the THV is partially self-expanded when a distal end region of the THV is larger by at least about 3 millimeters (mm) (or 5 mm, or 7 mm or other intermediate or larger values) above a diameter of the THV in the contracted state. The THV is moved relative to the sheath for full self-expansion of the THV for implantation, optionally when it is determined that the first anatomical location is the target anatomical location for implantation of the THV.

An aspect of some embodiments of the present invention relates to a delivery system for delivery of a self-expandable THV to an anatomical location within a heart of a patient. The delivery system includes an expansion controller for controlling expansion and re-collapse of the self-expandable THV. The expansion controller includes a mechanism for changing an operator applied rate of axial distal displacement or proximal displacement of a capsule housing the self-expandable THV for expanding or re-collapse of the self-expandable THV, to another rate of axial distal displacement or proximal displacement of the capsule for expanding or re-collapse of the self-expandable THV that is different than the operator applied rate.

An aspect of some embodiments of the present invention relates to a delivery system for delivery of a self-expandable THV to an anatomical location within a heart of a patient. The delivery system includes a shaft assembly including a shaft sized and/or shaped for delivery of the THV. The shaft assembly includes a capsule and a nose element. The capsule is sized and/or shaped for housing the self-expandable THV in a contracted state. The nose element may be sized and/or shaped as a cone located at a distal end region of the shaft in proximity to the capsule. The cone has a length of less than about 6 mm.

An aspect of some embodiments of the present invention relates to a delivery system for delivery of a self-expandable THV to an anatomical location within a heart of a patient. The delivery system includes a shaft assembly including a shaft sized and/or shaped for delivery of the THV. The shaft assembly includes a capsule and a nose element. The capsule is sized and/or shaped for housing the self-expandable THV in a contracted state. The nose element may be sized and/or shaped as a rounded dome located at a distal end region of the shaft in proximity to the capsule. A length of the rounded dome is less than about 4 mm. A radius and/or a shape of the rounded dome may substantially match an inner radius and shape of the capsule.

An aspect of some embodiments of the present invention relates to a delivery system for delivery of a self-expandable THV to an anatomical location within a heart of a patient. The delivery system includes a shaft assembly including a shaft sized and/or shaped for delivery of the THV. The shaft assembly includes a capsule and a nose element. The capsule and/or the nose element include an inner channel through which the stiff guidewire is threaded. The capsule and/or the nose element are designed such that a distal part of the nose can adjust its pose, optionally swivel freely, relative to the capsule. The nose element includes an aperture (e.g., fenestration) through which the guide wire passes. The aperture of the nose element has an eccentric shape, designed to accommodate the guidewire passing through the aperture for different poses of the nose element, for example, to reduce or avoid the guidewire pressing against tissues and/or reducing or avoiding sharp curves of the guidewire that contact tissues (which may damage the tissues, as described herein). Alternatively or additionally, the fenestration within the nose element is located at an eccentric location(s), selected to accommodate the guidewire passing through the aperture for different poses of the nose element. The design of the nose element and/or capsule to enable changes in pose (e.g., swivel) of the nose element and/or the eccentric shape of the guidewire exit port on the nose element may enable reducing risk of damage to internal tissues of a heart (e.g., conduction system).

An aspect of some embodiments of the present invention relates to a delivery system for delivery of a THV to an anatomical location within a heart of a patient. The delivery system includes a shaft assembly including a shaft sized and/or shaped for delivery of the THV. The shaft assembly includes a capsule, a nose element, and a nose release mechanism designed for quick release of the nose element from the shaft assembly.

An aspect of some embodiments of the present invention relates to a method for treating a patient. In response to deploying a THV (e.g., self-expandable and/or balloon expandable) in a target anatomical location of a heart of the patient (e.g., transcatheter aortic valve for replacing a native stenotic aortic valve) using a catheter of a delivery system used to deliver and deploy the THV, the stiff guidewire over which the catheter is riding (and which was used to deploy the THV) is exchanged with a soft guidewire. The exchange may be done by leaving the catheter in place, withdrawing the stiff guidewire out of the body of the patient using a lumen of the catheter as a guide, and inserting the soft guidewire into the body of the patient using the lumen of the catheter as the guide. The soft guidewire may be inserted through the deployed self-expandable THV, into the left ventricle. The delivery system is from the body of the patient over the soft guidewire.

An aspect of some embodiments of the present invention relates to a method of treating a patient by implanting a first THV (e.g., self-expandable and/or balloon expandable) at a location within an aortic annulus selected to enable deployment of a second THV within the first deployed THV without dislodging the first THV from the location. Alternatively or additionally, the first THV is implanted such that a distal end of the THV is at least about 0 mm, or within about 3-10 mm, or 3-5 mm, or 3-7 mm, or 5-7 mm, or 5-10 mm, or other values from a plane defined as a bottom of cusps of the aortic valve in proximity to a left ventricle. The location of for implanting the first THV may be selected to reduce likelihood of future device migration from the implant location, which may be detrimental to the patient. The location for implanting the first THV may be selected to enable a second (or more) THV to be implanted within the first THV, safety, without significantly increasing risk of dislodgement and/or migration of the deployed THV(s).

An aspect of some embodiments of the present invention relates to a method of treating a patient by implanting a THV within a heart valve, optionally an aortic valve. A balloon is inflated within a heart valve of the subject. The balloon may be inflated within the aortic valve, which may be stenotic and/or calcified, for example for expanding the opening annulus of the aortic valve to enable implanting the THV. Alternatively or additionally, the balloon is inflated within a previously implanted THV. Alternatively or additionally, the balloon is inflated after implantation of the THV. The balloon is not moved during the inflation process and/or while the balloon is inflated. The balloon may be monitored for movement, for example, by monitoring images (e.g., fluoroscopic images) depicting the balloon for movement, and generating an alert when movement is detected (e.g., an audio message played on speakers, a pop-up message presented on a display, and and/or a visual marker indicating movement is overlaid on the image(s)).

An aspect of some embodiments of the present invention relates to a method of treating a patient by implanting a THV within a heart valve, optionally an aortic valve. The THV delivered within a capsule connected to a nose element. After a portion of the nose element passes the annulus, the nose element is released (e.g., as described herein) from the capsule such that the released nose element is configured for freely swiveling. The freely swiveling nose element may reduce or prevent damage to tissue of the heart, by the nose element itself and/or from the guidewire passing through the nose element. The nose element may be released when the proximal end, distal end, and/or region between the distal and/or proximal ends of the nose element is at the level of a plane defining the aortic annulus (i.e., a plane below the cusps of the aortic valve, towards the left atrium).

An aspect of some embodiments of the present invention relates to a method of treating a patient by using a device which is passed into and/or past an aortic valve. The device may be, for example, a THV for implantation into the aortic valve, and/or a balloon for inflation within the aortic valve. Prior to passing the device into and/or past the aortic valve, a catheter located in the left ventricle is proximally retracted out of the left ventricle and/or past the aortic valve. The catheter may be, for example, a contrast catheter such as a pigtail catheter, used to inject contrast into the left ventricle. In response to the catheter's retraction, the device is distally displaced into the left ventricle and/or past the aortic valve, and/or the balloon is inflated within the aortic valve. Alternatively or additionally, the catheter (e.g., contrast catheter) may be located in the cusp(s) of the aortic valve, for example used as a marker to indicate location of the aortic valve, which may not appear in fluoroscopic images (e.g., without contrast). The catheter is retracted from the cusp(s) of the aortic valve prior to passing the device through the aortic valve and/or prior to inflation of the device and/or passing the device. Alternatively or additionally, the catheter (e.g., contrast catheter) may be located in proximity to the aortic annulus, for example, within about 1 centimeter (cm), or about 2 cm, or about 4 cm, or other values, from the aortic annulus. The catheter is retracted to distance of at least about 1 cm, or about 2 cm, or about 4 cm, or other values from the aortic annulus prior to inflation of the device and/or passing the device. As used herein, the case of the catheter located in the cusps of the aortic valve may sometimes be interchanged with the case of the catheter located in proximity to the aortic annulus, for example, within about 1 centimeter (cm), or about 2 cm, or about 4 cm, or other values, from the aortic annulus.

An aspect of some embodiments of the present invention relates to a method of treating a patient by using a guidewire placed within an organ of a patient. The guidewire may be a stiff guidewire. The guidewire may be passed across an annulus of an aortic valve, and a distal end of the guidewire is located within a left ventricle of a heart, for example, the guidewire is used to pass a THV and/or delivery system for implantation within the aortic annulus. The guidewire is monitored for detecting curvature of the guidewire less than a threshold, for example, the threshold is about 0.6 mm, or 0.8 mm, or 1.0 mm, or 1.2 mm, or other values. When the guidewire is detecting as having a region with a curvature below the threshold, the guidewire may be manipulated to increase the curvature to above the threshold. The threshold may be selected as indicating a sharp curvature with risk of damaging tissues by pressure applied by the sharp curvature. Increasing the curvature may reduce or prevent risk of damage to the tissues.

At least some embodiments described herein address the medical problem of tissue damage, for example, a conduction block, occurring after a transcatheter aortic valve replacement (TAVR). A pacemaker may be implanted to treat the conduction block. Inventors discovered that the conduction blocks occur after a self-expandable aortic valve, that is in a partially expanded state, is moved, for example, distally displaced further into the heart and/or proximally displaced in a direction away from the heart. In other words, the conduction blocks occurs when the self-expandable aortic valve is moved when not fully closed. Inventors hypothesize that that movement of the metal (e.g., Nitinol) stent of the self-expandable aortic valve against the tissues of the heart damages the conduction system within the tissues, for example, struts of the stent scratch and/or scrape the tissues thereby damaging the conduction system. At least some embodiments described herein improve the medical field of transcatheter valve replacement, optionally TAVR. The improvement is in the reduction of likelihood of conduction blocks after the transcatheter valve replacement, which may require insertion of a pacemaker. At least some embodiments described herein improve upon existing approaches of transcatheter valve replacement, optionally TAVR. The instructions for use (IFU) of the self-expandable aortic valve permit movement of the partially expanded self-expandable aortic valve in a partially expanded state and partially compressed state, which reinforces movement of the partially expanded self-expandable aortic valve as routine medical practice. Movement of the partially expanded self-expandable aortic valve is done, for example, to fine tune the specific location for deployment of the remainder of the valve. It is easier to visualize the partially expanded self-expandable aortic valve in fluoroscopic images (optionally with administered contrast), which helps the physician to select the specific location for expansion of the remaining part of the valve.

At least some embodiments described herein improve the aforementioned medical problem, and/or the aforementioned medical field, and/or the aforementioned existing medical practice, by prohibiting movement of a self-expandable transcatheter heart valve which is in a partial expanded state and a partial contracted state, thereby preventing or reducing likelihood of conduction blocks after the transcatheter heart valve replacement procedure which may require implantation of a pacemaker. Throughout the procedure, the self-expanded portion of THV is not moved within the heart and/or relative to the aortic valve. Movement of the self-expandable transcatheter heart valve is allowed in the contracted state and prohibited in the expanded state. When the self-expandable transcatheter heart valve is in the partial expanded state and the partial contracted state, the operator (e.g., physician) re-collapses the partially expanded portion to the contracted state, such that the entire valve is in the contracted state. The fully contracted valve may then be moved, and expanded.

At least some embodiments described herein address the medical problem of tissue damage, for example, a conduction transient or permanent conduction blocks, occurring after a transcatheter aortic valve replacement (TAVR). A transient or permanent damage to the heart conduction system may be caused and in some cases the conduction block requires the implantation of a pacemaker may be implanted to treat the conduction block. At least some embodiments described herein improve the technology of delivery systems, by providing a delivery system for delivery of a THV designed to reduce risk of damage to heart tissue, optionally to conductive tissue of the heart, which may reduce likelihood of transient or permanent damages to the heart conduction system some of which requiring a pacemaker after the THV implantation procedure. At least some embodiments described herein provide a solution to the aforementioned technical problem, and/or improve the aforementioned technology, by the expansion controller with mechanism for changing an operator applied rate of axial distal displacement or proximal displacement of a capsule housing the self-expandable THV for expanding or re-collapse of the self-expandable THV, to another rate of axial distal displacement or proximal displacement of the capsule for expanding or re-collapse of the self-expandable THV that is different than the operator applied rate. The rate of displacement by the expansion controller may be selected to be safer than the operator applied rate, for reduced likelihood of damaging the tissue. In other embodiments, the nose element of the shaft assembly is shaped as a cone having a length of less than about 6 mm, for reducing risk of damage to heart tissue. In yet other embodiments, the nose element of the shaft is shaped as a swiveling dome with an eccentric port for the guidewire exit, for reducing risk of damage to heart tissue.

At least some embodiments described herein address the medical problem of tissue damage, for example, a conduction block, cardiac tamponade, and/or other damage to tissues of the heart. The tissue damage may occur from inadvertent motion of a stiff guidewire which was used to guide the catheter of the delivery system for implantation of the self-expandable THV. At least some embodiments described herein address the medical field of implantation of THV and/or the medical field of improving patient safety. During a phase of extraction of the catheter of the delivery device used to deploy the self-expandable THV (i.e., after the self-expandable THV has been deployed), the operator (e.g. physician, fellow, on-call doctor) performs certain steps, for example, guided by the instructions for use (IFU) of the self-expandable THV. The operator may center the distal end region of the catheter used to deliver the self-expandable THV and the stiff guidewire to the center of the deployed THV. This centering is done to protect the deployed THV from potential damaging forces that may applied by the stiff guidewire and/or the distal part of the delivery device when a distal region of the stiff guidewire is located in the left ventricle. The damaging forces may be, for example, an applied transverse rotation to the delivery device, which may damage the deployed THV and/or may damage the internal tissues of the heart (e.g., causing damage to the conduction system, cardiac tamponade, and the like). The operator may withdraw the stiff guidewire, such that the distal end region of the guidewire is positioned within the catheter of the delivery system. The catheter may then be pulled out of the body of the patient. However, since the motion of pulling the catheter out of the body may result in simultaneous retraction of the stiff guidewire, the operator may retract the catheter while simultaneously distally displacing the stiff guidewire back into the left ventricle. Sometime the two opposing movements (i.e., the proximal retraction of the catheter and the distal displacement of the stiff guidewire) are not coordinated sufficiently. This may cause, for example, the stiff guidewire to be released above (i.e., antegrade to) the THV which may damage the deployed THV and/or may damage tissue in proximity (e.g., conduction tissue). This may cause, for example, the stiff guidewire to be pushed forcefully into the interior tissue of the LV, which may lead, for example, a conduction block, cardiac tamponade, and/or other damage. At least some embodiments described herein address the aforementioned medical problem and/or improve the aforementioned medical field, by exchanging the stiff guidewire with the soft guidewire prior to removal of the catheter from the body. The exchange may eliminating the step of withdrawing the stiff guidewire prior to the extraction of the catheter.

At least some embodiments described herein address the medical problem of tissue damage, for example, a conduction block. Inventors discovered that moving the balloon during inflation and/or while inflated may lead to damage of heart tissue, for example, damage to the conduction tissue of the heart. Damage may occur, for example, from shear forces and/or pressure applied by the balloon on the heart tissue. At least some embodiments described herein that prevent movement of the balloon while inflated and/or during inflation may avoid or reduce risk of damage to the heart tissue.

At least some embodiments described herein address the medical problem of tissue damage, for example, a conduction block. Inventors discovered that the nose element passing through the annulus may damage heart tissue, for example, the nose element is too long and contacts the heart tissue after passing through the annulus (e.g., inside the left ventricle), the nose element is too sharp and damages tissue when contacting the tissue, and/or the guidewire (e.g., stiff) passing through the nose element applies pressure to the issue. At least some embodiments described herein solve the medical problem, by a short nose element (so that the nose element doesn't contact the inner tissue of the left ventricle after passing through the annulus), a nose element that is dome shaped (i.e., not sharp), a nose element that is capable of being released, a nose element that is capable of swiveling, and/or a nose element having an eccentric aperture. The release and/or the freely swiveling nose element may reduce or prevent damage to tissue of the heart by the nose element itself and/or from the guidewire passing through the nose element. The eccentric aperture of the nose element may reduce pressure on the guidewire that is applied to the inner tissue of the heart which may reduce risk of damage to the heart tissue.

At least some embodiments described herein address the medical problem of enabling placing a second (or more) THV in a previously implanted THV, such as after the initially implanted THV has malfunctioned (e.g., after about 7-10 years). At least some embodiments described herein solve the medical problem, by implanting the initial THV such that the distal end of the THV is past the aortic annulus (e.g., plane defining the lower part of the cusps towards the left ventricle), greater than 0 mm, such as greater than about 1, 3, 5, 7, 10 mm, or other values as described herein. The distal portion of the THV that enters the left ventricle, past the aortic annulus, may provide mechanism support for implantation of a second (or more) THV within the previously implanted THV.

At least some embodiments described herein address the medical problem of expanding and contracting the THV multiple times during the THV implantation procedure, when the THV cannot be moved when expanded and cannot be moved when partially expanded, as described herein. Expanding and contracting the THV using standard approaches takes time, and/or may be cumbersome. At least some embodiments described herein provide a solution to the medical problem, by using the expansion controller described herein that is designed to quickly expand and/or contract the THV, even multiple times. The expansion controller reduces the time and/or simplifies the tasks of expanding and contracting the THV for the operator.

At least some embodiments described herein address the medical problem of tissue damage, for example, a conduction block. The tissue damage may occur when a device (e.g., THV and/or delivery system) is passed into and/or past an aortic valve, while a second catheter (e.g., contrast catheter, pigtail catheter) is located in the left ventricle and/or while the second catheter is located in cusp(s) of the aortic valve (e.g., used as a marker). At least some embodiments described herein provide a solution to the medical problem, by proximally retracting the second catheter out of the left ventricle and/or past the aortic valve and/or out of the cusp(s). Once the second catheter has been retracted, the device may be passed through and/or into the aortic annulus.

At least some embodiments described herein address the medical problem of tissue damage, for example, a conduction block. The tissue damage may occur by a tight curved region of a guidewire (e.g., stiff guidewire) applying pressure against tissue, for example, during a THV replacement procedure the tight curves region applies pressure against the aortic annulus and/or interior of the left ventricle. At least some embodiments described herein provide a solution to the medical problem, by monitoring the guidewire for tight curves, and manipulating the guidewire to increase the curvature.

At least some features described herein may be implemented by adapting existing instructions for use (IFU) of THVs, optionally for replacing of aortic valves.

Inventors discovered that certain clinical scenarios may result in conduction blocks, for example increase QR duration, blocked P wave (that is disconnected from the QRS), change in direction of the QRS axis (e.g., right or left shift of QRS axis), and the like. Conduction blocks may be temporary, and/or require temporary pacing and/or monitoring. Conduction blocks may require pacing during the procedure. Conduction blocks may be permanent, requiring implantation of a pacemaker. Inventors analyzed videos and/or other data of THV procedures. When ECG monitoring the subject indicated a change, for example, ECG signals indicating a conduction block appear, Inventors viewed the corresponding video and/or data that occurred during the ECG change and/or right before, in an attempt to discover the cause. The following are examples of some scenarios analyzed by Inventors, and corresponding embodiments described herein that may reduce or prevent conduction disturbances:

Moving a THV when expanded, or partially expanded, for example, a distal end of the THV is at least greater than about 3 mm (or other value) from the THV in the contracted state, lead to a conduction block. The conduction block may occur when the expanded distal portion of the THV is distally displaced, for example, the ends of the metal stent of the THV scratch and/or apply shear forces against tissue. The THV may be self-expanded. At least some embodiments described prohibit moving of the THV when expanded or partially expanded, for reducing or avoiding risk of conduction block. One or more of proximal movement and distal movement are prohibited.

Moving a balloon in the aortic valve while the balloon is inflated, lead to a conduction block. The balloon was inflated prior to implanting the THV, in a stenotic aortic valve, to break calcifications and/or expand the opening size of the malfunctioning aortic valve to enable deployment of the THV. At least some embodiments described herein prohibit moving of the balloon while in the aortic valve during inflation and/or while the balloon is inflated, for reducing or avoiding risk of conduction block.

Inflating a balloon while another catheter (e.g., non-THV catheter such as a contrast injection catheter, such as a pigtail catheter) is located in the left ventricle and/or in the cusp(s) of the aortic valve is prohibited. Inventors discovered that the balloon, when inflated, applies pressure to the non-THV catheter, which applies pressure to the tissue, which may cause the conduction block. At least some embodiments described herein indicate that the non-THV catheter is to be removed from the left ventricle and/or cusp(s) prior to inflation of the balloon.

When a stiff guidewire that passes though the delivery device used to deliver the THV is pushed distally and bends, the stiff guidewire contracts tissue with high force, leading to a conduction block. At least some embodiments described herein are directed to one or more of the following: releasing the nose element after passing through the aortic annulus, design for swiveling nose element, eccentric aperture of nose element, and/or replacing the stiff guidewire with a soft guidewire for retrieval of the delivery system outside the body of the patient, are for reducing or avoiding risk of conduction block.

When a stiff guidewire is inserted into the left ventricle, through the aortic annulus of the aortic valve, a region of the guidewire having a high curvature may press against tissue of the heart and apply high localized pressure. The high curved region may apply high pressure sufficient to damage tissues, causing the conduction block. At least some embodiments described herein monitor for regions of the guidewire with high pressure, and increase the curvature of the guidewire, for example, by manipulating the guidewire. Eliminating highly curved regions may avoid or reduce conduction disturbances, by reducing the pressure applied by the guidewire to the interior of the heart to a level where the pressure does not damage tissues. Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
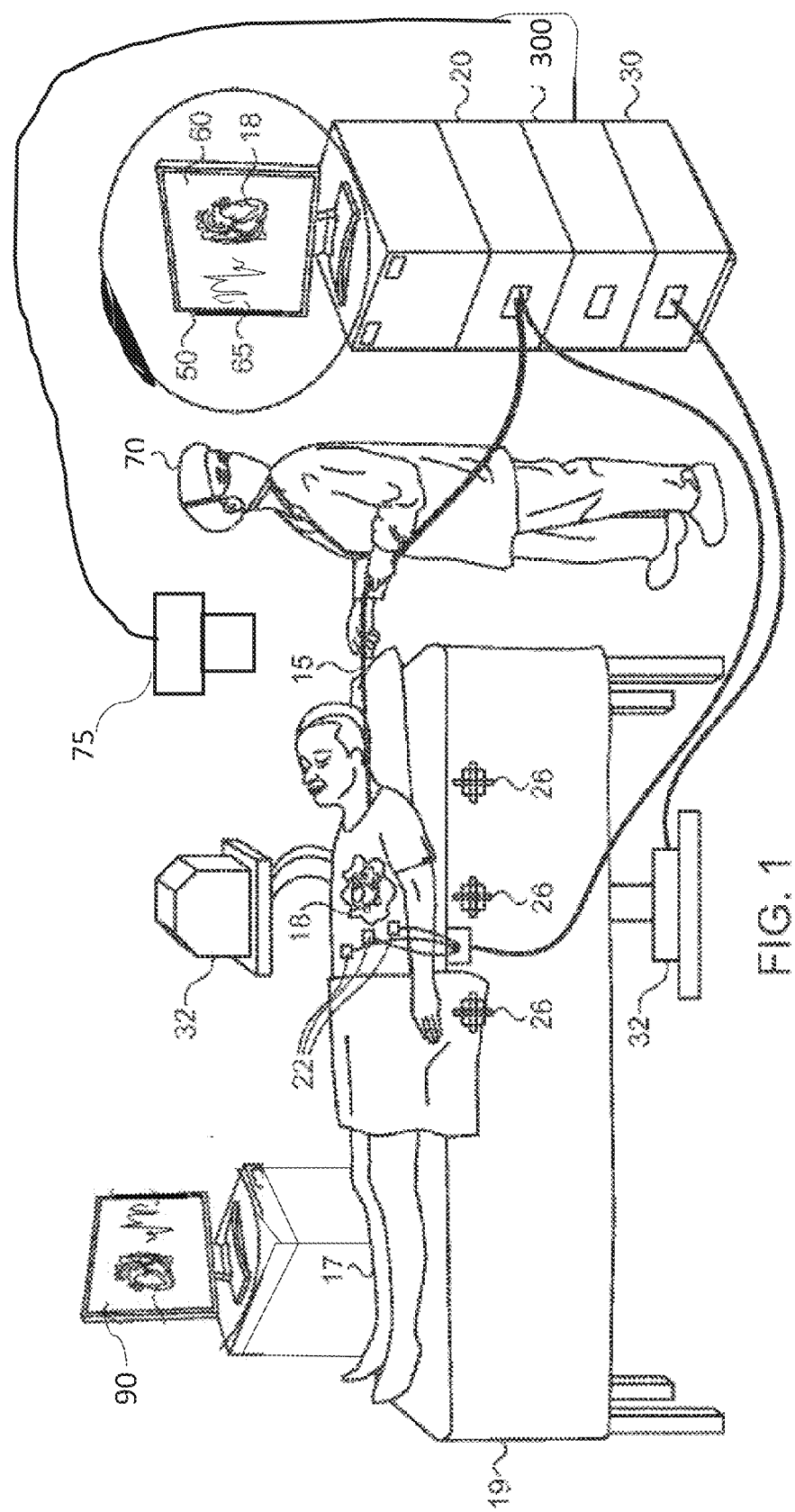
FIG. 1 is a schematic, pictorial illustration of an operating room equipped with a system for guiding a THV replacement procedure, in accordance with an embodiment of the present invention.
Figure 2:
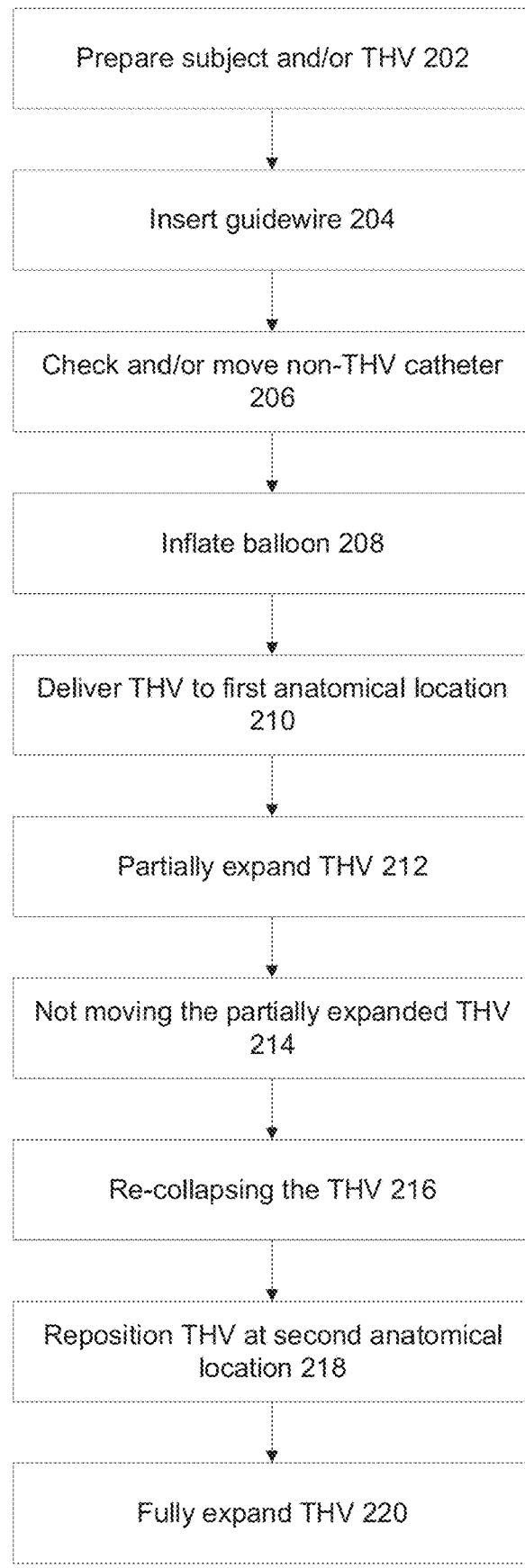
FIG. 2 is a flowchart of a method of treating a patient by delivering a THV to a heart of the patient, in accordance with some embodiments of the present invention.
Figure 3A:
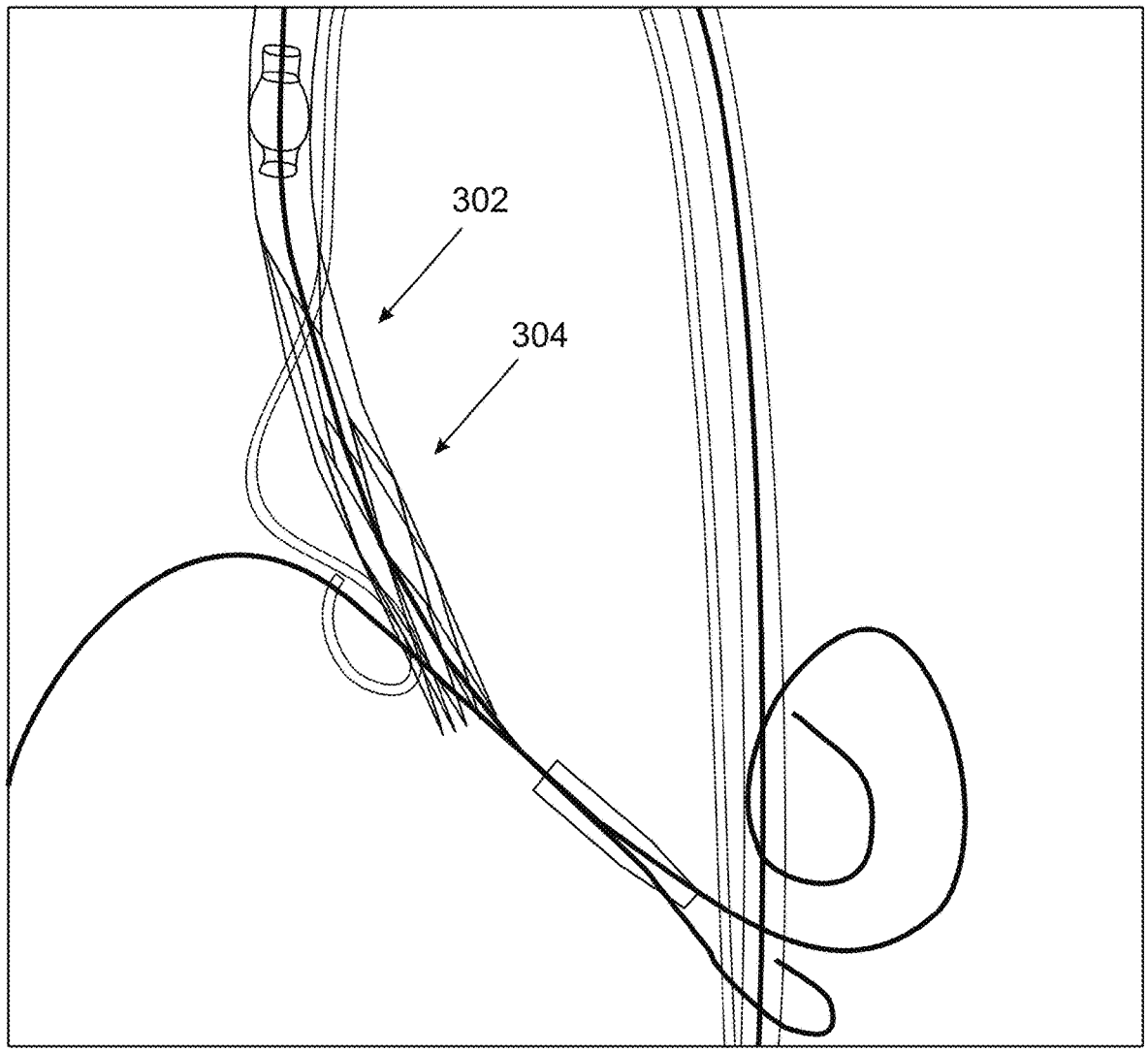
FIGS. 3A-3C are schematics depicting an expandable THV within a heart of a subject for implantation, in accordance with some embodiments of the present invention.
Figure 3B:
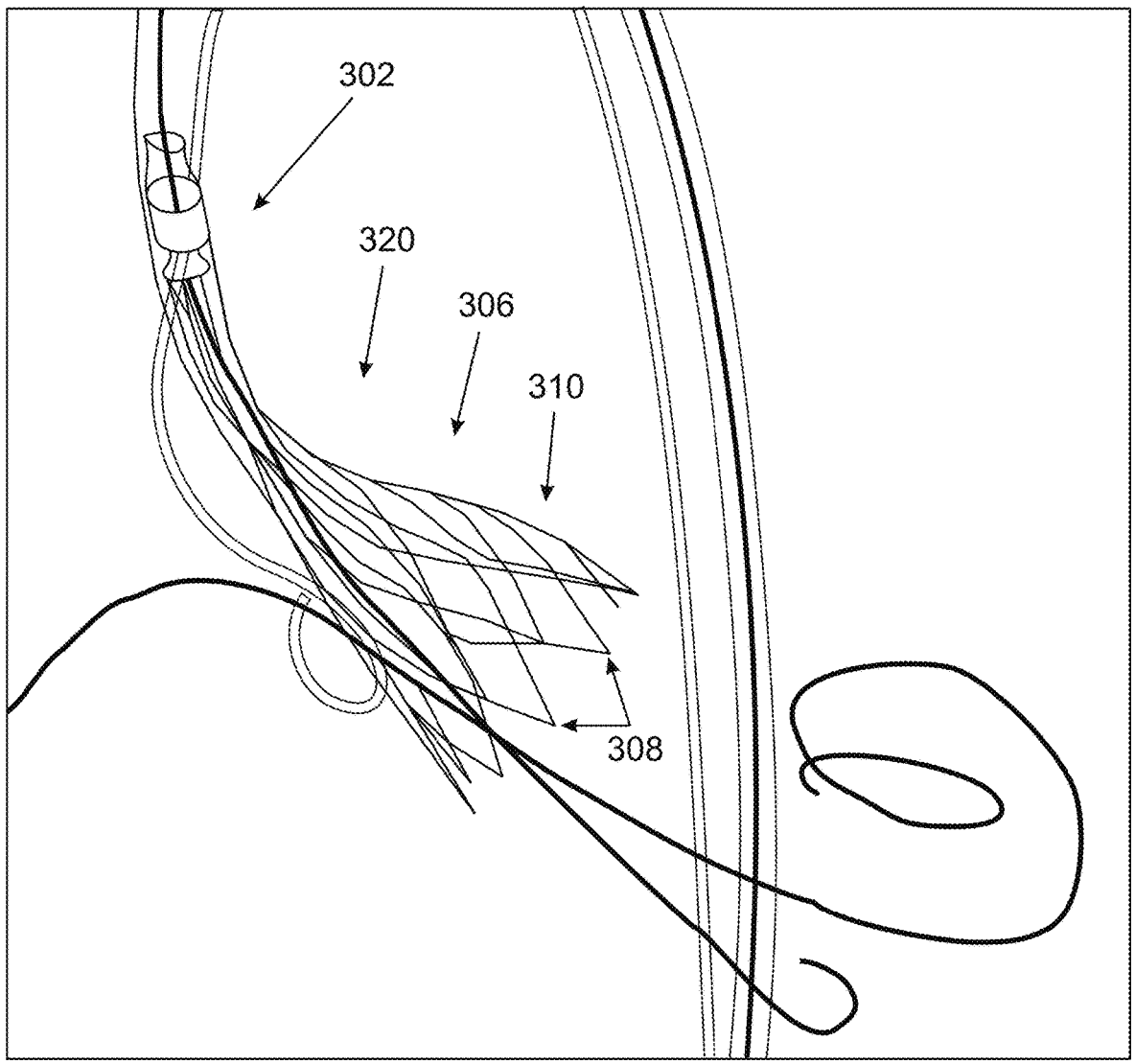
Figure 3C:
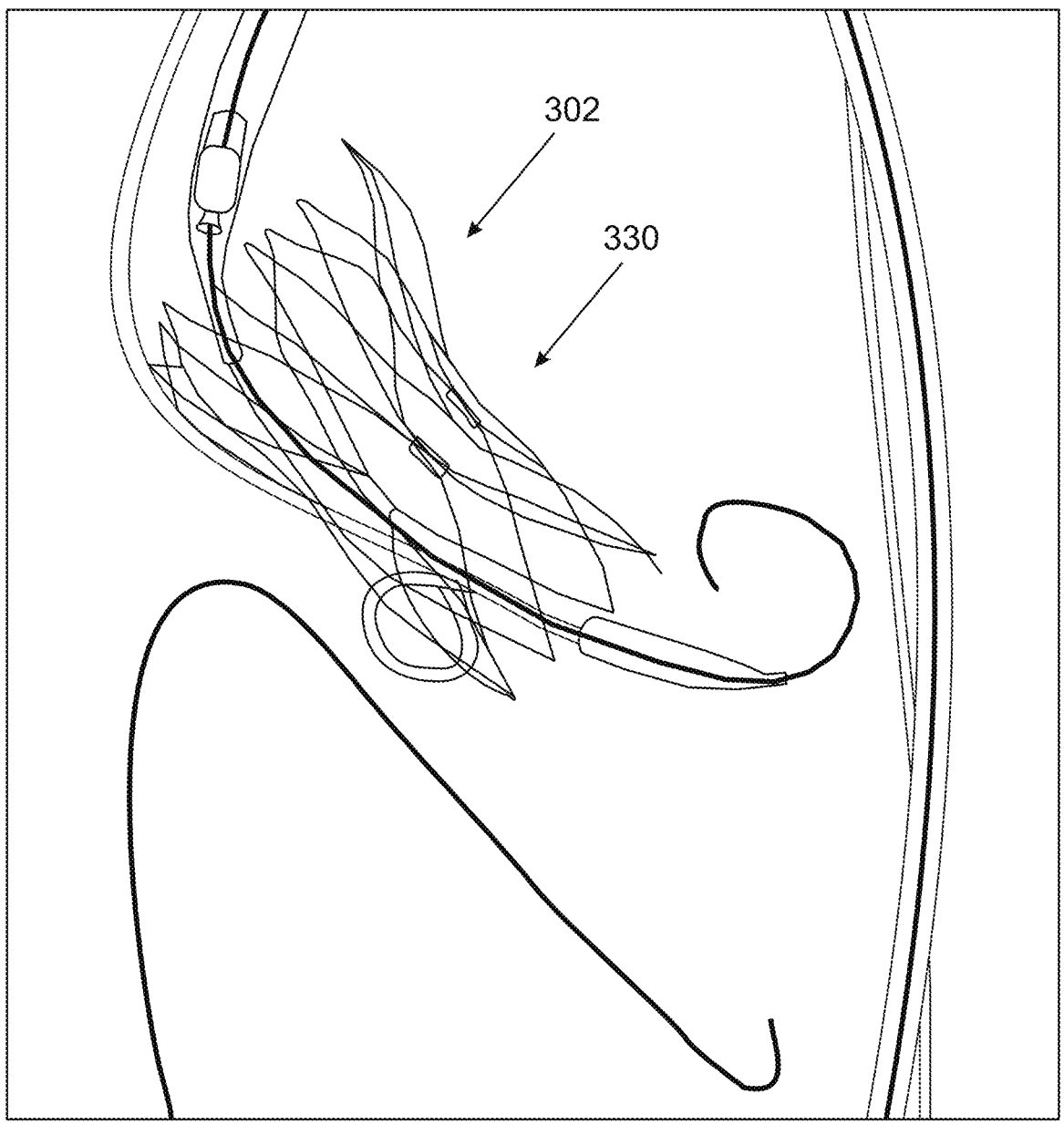
Figure 4:
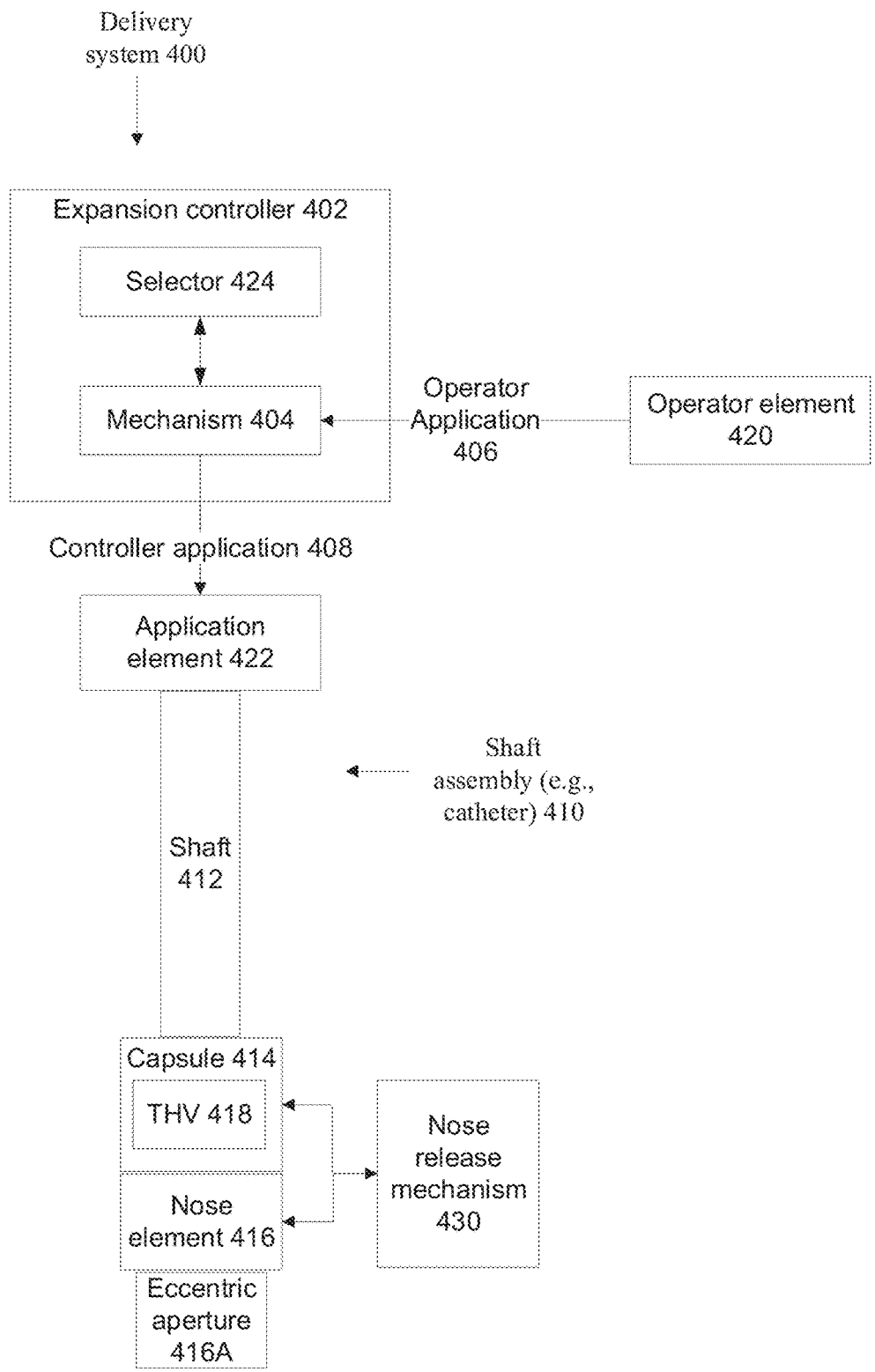
FIG. 4 is a schematic of a delivery system for delivery of a THV for reducing risk of damage to heart tissue, in accordance with some embodiments of the present invention.

Reference is now made to FIG. 1, which is a schematic, pictorial illustration of an operating room equipped with a system 300 for guiding a THV replacement procedure, in accordance with an embodiment of the present invention. Reference is also made to FIG. 2, which is a flowchart of a method of treating a patient by delivering a THV to a heart of the patient, in accordance with some embodiments of the present invention. Reference is also made to FIGS. 3A-3C, which are schematics depicting a self-expanding THV within a heart of a subject for implantation, in accordance with some embodiments of the present invention. Reference is also made to FIG. 4, which is a schematic of a delivery system 400 for delivery of a THV 418 for reducing risk of damage to heart tissue, in accordance with some embodiments of the present invention. Reference is also made to FIGS. 5A-5E, which include schematics of separating a nose element 416 from a capsule 414 passed over a guidewire 550, in accordance with some embodiments of the present invention. Reference is also made to FIG. 6, which is a method of exchanging a stiff guidewire with a soft guidewire, in accordance with some embodiments of the present invention.

Referring now back to FIG. 1, system 300 is depicted as being used for guiding a transcatheter valve replacement, for example, deployment of a self-expanding aortic valve. A catheter 15 is percutaneously inserted into a living body 17 of a patient lying on a gurney 19. Catheter 15 is part of a delivery system for delivering and deploying the self-expanding THV, for example, as described with reference to FIG. 4 and/or FIG. 6. Catheter 15 is controlled and manipulated by operator 70. Catheter 15 may be connected to an expansion controller 20 as the catheter is navigated into a heart 18 of the patient. Embodiments of expansion controller 20 are described herein.

Electro-cardiac signal (ECS) probe sensors 22 may be attached to the surface of patient body 17 optionally near heart 18 in order to receive electro-cardiac signals. Probe sensors 22 may exemplify monitoring sensors that monitor physiological state of patient body 17, e.g., by monitoring its ECG (body surface and/or intra-cardiac).

In some embodiments, e.g., in embodiments using the CARTO™ system for mapping and navigation, one or more magnetic field generators 26 may create a magnetic field through the body of the patient, for use by the CARTO system to track the position of catheter 15 in heart 18. The CARTO system (Biosense Webster, Diamond Bar, Calif.) is described, for example, in International patent application publications Nos. WO2018/130974, WO2019/034944, WO2019/035023, and WO/2020/008418.

In some embodiments, an imaging system 30 may be used to obtain images of the heart. Imaging system 30 is shown to include an imaging source 32, which may use magnetic resonance imaging (MRI), X-ray computed tomography (CT), fluoroscopy or any suitable imaging technique to obtain images of the heart image. The image of the heart may be digitized and stored in imaging system 30.

Images captured by imaging system 30 may be displayed to operator 70 on an output display 60 on a monitor 50.

The position of the catheter distal end region that includes the self-expanding THV as depicted in images captured by imaging machine 32 may be displayed to operator 70 on output display 60 on monitor 50.

Optionally, a camera 75 may monitor a proximal portion of a guidewire over which catheter 15 and/or THV are delivered into the heart, and/or camera 75 may monitor a proximal portion of catheter 15. Images of camera 75 may be analyzed to detect motion of catheter and/or guidewire when the partially deployed THV and/or the guidewire are to remain in a substantially constant position, as described herein.

System 300 may receive heart images from imaging system 30, and may receive ECG signals (and/or other physiological parameters of the patient body) from the local electro-cardiac signals obtained from sensors 22, and/or the catheter location obtained from navigating system 20, and/or a video recording of the proximal portion of the catheter and/or guidewire from camera 75. System 300 may analyze and/or present the images, as described herein.

System 300 may be designed to receive a user input from operator 70. Operator terminal 50 may include a display 60 and/or a user input device, such as a keyboard, mouse, touchscreen, a microphone connected to a speech to text application, etc. In some embodiments, display 60 is a touch-screen that allows the operator to input requests or other data to system 300. Display 60 is shown to display heart 18 and a signal 65 received from sensors 22.

The operating room may further include one or more displays 90 (one is shown) that display the output from the monitoring, tracking, and/or imaging systems directly, i.e., not via system 300. For example, one or more displays 90 display the signals received in real time, even when display 60 shows different data.

Referring now back to FIG. 2, one or more features of the method may be performed by one or more human operators (e.g., interventional cardiologists, fellows) and/or automatically such as by a robot. The robot may perform a portion of the procedure or the whole procedure.

Throughout the medical procedure of implanting the THV, includes features described with reference to FIG. 2, when the THV is at least partially expanded within the heart (e.g., within the aortic annulus), the partially expanded THV is prohibited from being moved (i.e., no moved) within the heart, optionally not moved relative to the valve being replaced (e.g., aortic valve), for example, not proximally displaced (e.g., antegrade), not distally displaced (e.g., retrograde), and/or not rotated.

At 202, a subject (also referred to herein as a patient) is prepared using the procedure, for example, laid down on the table, the access site is sterilized, access to the blood vessel is obtained, and the like. The THV may be selected and/or prepared, for example, rinsed with saline, compressed, loaded into a delivery system, and the like.

The patient may be suffering from a medical condition which is treatable by using a transcatheter valve, optionally a transcatheter heart valve, optionally a self-expanding transcatheter heart valve, for example, made out of a memory material such as Nitinol. The self-expanding THV may include a biological material (e.g., bovine heart valve) and/or a synthetic material (e.g., polyurethane, polytetrafluoroethylene (PTFE), and the like).

In an example, the patient suffers from a non-healthy aortic heart valve, optionally an aortic valve. For example, the patient suffers from aortic stenosis that is associated with a clinical indication for aortic valve replacement. The patient may be treated using a transcatheter aortic valve replacement (TAVR) procedure for replacing the non-healthy aortic heart valve with a transcatheter aortic valve.

In another example, the patient suffers from a previously implanted artificial heart valve that has malfunctioned, for example, a previously deployed self-expandable aortic valve that has malfunctioned. The patient may be treated by deploying a second THV in the previously implanted artificial heart valve that has malfunctioned.

At 204, the guidewire used for passing the THV into the left ventricle is inserted into the body of the patient. The guidewire may be used for passing a balloon for pre-inflation of the native valve and/or the previously implanted THV.

The guidewire is inserted prior to passing the THV over the guidewire.

The guidewire may be a stiff guidewire.

During the insertion of the guidewire, a native heart valve (e.g., aortic valve) or a previously deployed prosthetic valve (e.g., THV, aortic valve) may be crossed without a loop of the guidewire. The native heart valve (e.g., aortic valve) and/or the previously deployed prosthetic aortic valve (e.g., THV, aortic valve) may be avoided with the loop of the guidewire.

Optionally, during the insertion of the guidewire (e.g., stiff guidewire) and/or throughout the procedure, the guidewire may be monitored for detecting formation of one or more curves at regions of the guidewire. The curves may be monitored to detect whether the curves are tight Optionally, tight curves of the guidewire are prevented and/or not reached and/or reduced. A tight curve may have a local radius above a threshold. Curves below the radius may be considered as not tight. Tight curves may represent risk of damage to tissue, for example, the tight curve represents a region of high pressure that can damage tissues. The threshold may be about 0.6 millimeters (mm), or 0.8 mm, or 1.0 mm, or 1.2 mm, or 1.4 mm, or other smaller, intermediate, or larger values. I.e., Curve of the guidewire below about 0.6 mm, or 0.8 mm, or 1.0 mm, or 1.2 mm, or 1.4 mm, or other smaller, intermediate, or larger values are avoided. The guidewire may be monitored to detect tight curves, for example, by analyzing the guidewire on fluoroscopic images, and dynamically measuring curvature of the guidewire, optionally at regions contacting tissues. When a region of the guidewire having a curve below the threshold is detected, an alert may be generated, for example, an audio message played on speakers and/or a visual indication presented on the display. The guidewire may be manipulated for increasing the curvature above the threshold, for example, rotating the guidewire, proximally displacing the guidewire, and/or distally displacing the guidewire. Other approaches for increasing the curvature may be used.

At 206, a non-THV catheter, for example, a contrast administration catheter, such as a pigtail catheter, may be located in the heart of the subject (i.e., having been previously inserted). The non-THV catheter may be located in the left ventricle and/or in cusp(s) of the aortic valve (e.g., serving as a marker to indicate location of the aortic valve on non-contrast fluoroscopic images).

A check may be performed to determine whether the non-THV catheter (e.g., contrast catheter, pigtail catheter) is positioned between aortic valve cusps of the native aortic valve. For example, images with and/or without injected contrast are analyzed. The images may be fluoroscopic images capturing in real time during the procedure. The analysis may be a manual visual analysis by a human and/or automatic analysis by a processor executing image analysis code such as by feeding the images into a trained machine learning model (e.g., neural network).

When the non-THV catheter is found to be positioned between the aortic valve cusps of the native aortic valve, the balloon is not expanded (i.e., inflated). The position of the non-THV catheter between the aortic valve cusps of the native aortic valve may lead to tissue damage when a balloon is inflated within the annuls of the native aortic valve. The tissue damage may be caused by pressure applied by the balloon to the non-THV catheter against tissue located between the aortic valve cusps. The tissue damage may include damage to the conduction system of the heart, for example, to the bundle of HIS and/or to the atrioventricular (AV) node.

Prior to inflation of the balloon and/or prior to passing the THV (or another device) through the aortic annulus, the non-THV catheter is moved away from sensitive tissues that may be damaged by compression of the balloon against the non-THV catheter, for example, tissues of the conduction system of the heart.

When the non-THV catheter is found to be positioned between the aortic valve cusps or in the vicinity of the native aortic valve, the non-THV catheter may be moved to another suitable location prior to inflating the balloon, optionally a left coronary cusp, or optionally a way from vicinity to the aortic valve. The non-THV catheter may be moved from tissues being compressed by expansion of the balloon during inflation to the other suitable location in which risk to tissue damage (e.g., conduction system) is reduced or eliminated, optionally the left coronary cusp. The left coronary cusp may be furthest away from the bundle of HIS and/or AV node which may be damaged by compression of the non-THV catheter, thereby reducing or preventing risk of damage to the bundle of HIS and/or AV node. The balloon may be expanded (i.e., inflated) in the new location. Moving the non-THV catheter pigtail reduces or avoids conduction system damage by the expanding balloon applying pressure to the non-THV catheter against tissue.

Alternatively or additionally, the non-THV catheter is located within the left ventricle. Prior to passing the THV and/or balloon (or other device) into and/or past an aortic valve, the non-THV catheter located in the left ventricle is proximally retracted out of the left ventricle and/or past the aortic valve. In response to the retraction of the non-THV catheter, the balloon and/or THV and/or other device is distally displaced into the left ventricle and/or past the aortic valve.

At 208, the balloon may be delivered over the guidewire to the native valve (e.g., aortic valve) and/or to the previously implanted THV (where a new THV is to be positioned within the previously implanted THV).

Optionally, a substantially constant location of a distal end region of the guidewire is maintained while the balloon is being delivered over the guidewire, and/or while the balloon is being removed over the guidewire (e.g., while the balloon is removed from a location where the balloon was inflated, optionally to be removed outside the body).

The balloon may be inflated within the native valve (e.g., aortic valve) and/or within the previously implanted THV in which the THV is to be deployed. The inflation may be performed prior to passing the self-expandable THV over the guidewire.

Optionally, the balloon is not moved during the inflation. Alternatively or additionally, the inflated balloon is move moved while inflated, including the fully inflated state where the balloon is not additionally inflated. The balloon may not be distally displaced (e.g., pushed forward) and/or proximally displaced (e.g., pulled backwards).

The balloon may be inflated within an aortic valve, which may be stenotic and/or calcified, for example for expanding the opening annulus of the aortic valve to enable implanting the THV. Alternatively or additionally, the balloon is inflated within a previously implanted THV. Alternatively or additionally, the balloon is inflated after implantation of the THV (e.g., after full expanding the THV as described with reference to 220). The balloon is not moved during the inflation process and/or while the balloon is inflated.

The balloon may be monitored for movement, for example, by monitoring images (e.g., fluoroscopic images) depicting the balloon for movement, for example, by comparing the location of the balloon between successive images, such as by optical flow and/or by subtracting images from each other, to detect distal and/or proximal displacement of the balloon. Alternatively or additionally, the guidewire of the balloon may be monitored to detect distal and/or proximal displacement, for example, by monitoring a marker on the guidewire, optionally outside the body of the patient. An alert may be generated when movement is detected (e.g., an audio message played on speakers, a pop-up message presented on a display, and and/or a visual marker indicating movement is overlaid on the image(s)).

The balloon may be placed at an initial position within the native valve and/or within the previously implanted THV prior to the beginning of inflation. Once inflation has commenced, the balloon may not be moved from the initial position during the inflation. Movement of the inflating balloon and/or inflated balloon may apply a shear force to the tissue that may damage the tissue, for example, damage to the conduction system, such as the bundle of HIS and/or AV node. Avoiding movement of the balloon reduces or prevents damage to the tissue (e.g., conduction system).

At 210, the self-expandable THV is delivered over a guidewire and within a sheath to a first anatomical location within the heart.

The first anatomical location may be a best attempt to reach the target anatomical location within the heart in which to deploy the THV. The target anatomical location may be, for example, within the annulus of the native valve (e.g., aortic valve) and/or within the previously implanted THV. Reaching the target anatomical location during the first attempt may not be successful, for example, due to difficulty in visually identifying the specific target anatomical location on images (e.g., fluoroscopic images), and/or due to movement of the THV and/or delivery system from blood flowing within the heart and/or due to shortening of the length of the THV as the THV is expanded. The determination of whether the first anatomical location is within the target anatomical location or whether the first anatomical location is different than the target anatomical location may be made by partial self-expansion of the THV and/or with injected contrast. When the first anatomical location is different than the target anatomical location, the self-expanding THV may be moved to another location (sometimes referred to herein as a second anatomical location) in an attempt to find the target anatomical location.

A substantially constant location of a distal end region of the guidewire may be maintained while the THV is being delivered over the guidewire. The distal end region of the guidewire may be maintained in the substantially constant location within the left ventricle, for example, by monitoring the location of the guidewire, including when devices are being delivered over the guidewire (e.g., sheath, THV, delivery system). The guidewire may be prevented from being displaced distally into the body (e.g., deeper into the left ventricle) and/or proximally (e.g., in a direction of being retracted from the body). The constant location of the guidewire may be maintained, for example, manually by the operator holding the portion of the guidewire located outside the body, and/or by a device that clamps the portion of the guidewire located outside of the body to prevent inadvertent displacement of the guidewire.

At 212, a portion of the THV is self-expanded within the first anatomical location. Another portion of the THV in the sheath remains in the contracted state.

The portion of the THV that is self-expanded is less than the full THV, for example, up to about 25%, or about 50%, or about 75% of the length and/or diameter of the THV is self-expanded.

The portion of the THV may be partially self-expanded when a distal end region of the THV (e.g., diameter) is larger by at least about 3 mm (or 5 mm, or 7 mm or other intermediate or larger values) above the diameter of the THV in the contracted state. In another example, the portion of the THV may be partially self-expanded when the distal end region of the THV (e.g., diameter) is larger by at least about 25%, or 50%, or 75%, or 100% above the diameter of the THV in the contracted state.

The portion of the THV may be partially self-expanded by moving the THV relative to the sheath, for example, retracting the sheath while maintaining the position of the THV, distally displacing the THV while maintaining the position of the THV, and/or a combination thereof where the sheath is retracted while distilling displacing the THV.

The self-expansion may occur in response to the THV being warned up by the surrounding blood, for example, when the scaffold of the THV is made from a memory material, such a memory metal, for example, Nitinol.

Optionally, the portion of the THV is self-expanded by starting release of a nose element after a distal end region of the nose element passed through an aortic annulus of an aortic valve in which the THV is to be implanted. The nose element is of the delivery system that is used to deliver the THV in the contracted state to the heart. Optionally, the THV is self-expanded by starting release of the nose element of the THV. Releasing the nose element enables independent movement of the nose element from movement of the rest of the delivery device housing the THV, which may prevent and/or reduce likelihood of heart tissue damage in the direction of delivery device movement.

Alternatively or additionally, the nose element is released after the distal end of the THV in the contracted state (optionally within the capsule and/or within the catheter) passes through the valve (e.g., aortic valve), optionally after the distal end of the THV passes through the opening of the aortic valve into the left atrium. The nose element may be released when the proximal end, distal end, and/or region between the distal and/or proximal ends of the nose element is at the level of a plane defining the aortic annulus. The nose element may be released, for example, using standard approaches and/or using a nose release mechanism designed for quick release of the nose element. Releasing the cone element may reduce the pulling force that the stiff guidewire exerts on the path of the THR, and reduces the effective length of the distal portion of the delivery device (e.g., capsule that houses the THV) to be closer to the length of the THV itself. Reducing the pulling force by the guidewire and/or reducing the effective length of the distal portion of the delivery device, by the release of the cone element, may improve maneuverability of the THV and/or may reduce the potential damage to the heart tissue. Maneuverability of the THV may be improved by the shorter length of the delivery device that houses the THV and/or by reduced resistance from the guidewire. Damage to heart tissue may be reduced, for example, by reduced risk of damage to tissues from the guidewire and/or by increased ability to more accurately position the THV at the target anatomical position.

At 214, the THV is not moved while the THV is in the partially self-expanded state.

Throughout the procedure, when the portion of the THV is at least partially expanded (i.e. in the partially self-expanded state) within the heart, optionally within the aortic annulus, the partially expanded THV is not moved with respect to the heart, optionally not moved relative to the valve being replaced (e.g., aortic valve). Movements of the portion of the THV that is at least partially expanded include, for example, not proximally displacing (e.g., antegrade), not distally displacing (e.g., retrograde), and/or not rotating, the portion of the THV that is at least partially self-expanded.

The partially self-expanded state may include any of the inflow struts of the THV protruding out of the sheath (e.g., protective sleeve). Alternatively or additionally, the partially self-expanded state may include when the distal end region of the THV (e.g., diameter) is larger by at least about 3 mm (or 5 mm, or 7 mm or other intermediate or larger values) above the diameter of the THV in the contracted state.

The THV is not distally displaced and not proximally displaced within the partially self-expanded state. It is noted that the prohibition of moving the THV while in the partially self-expanded state is in contrast to prior approaches, in which the THV is moved (e.g., distal displacement and/or proximal displacement) while in the partially self-expanded state, for example, in an attempt to position the THV in the target anatomical location.

The THV in the partially self-expanded state is not moved, even when no annular contact has been made. This is in contrast to prior approaches, which allow movement of the THV as along as annular contact has not been made, even when the THV is partially expanded The THV is not moved (e.g., advanced or withdrawn) once any of the inflow struts are exposed and/or protruding (e.g., from the sheath and/or capsule).

The THV may be moved (e.g., advanced or withdrawn) when the THV is completely within its sheath and in the contracted state.

Inventors discovered that the distance of the implanted THV (e.g., self-expandable THV and/or balloon expandable THV) relative to the aortic annulus is not related to induction of most of the conduction disturbances happening after TAVr. Inventor's discovery is opposite to the current understanding of the causes for conduction disturbances happening after TAVr. Furthermore, currently, most of the THV's IFUs recommend to implant the THV at the highest possible position within the aortic annulus, as close as possible to the aorta and/or furthest away from the left ventricle as possible. The THV is to be implanted adjacent and below to the aortic annulus, as close as the operator is able to get a safe secure anchoring position of the THV to the left ventricular outflow tract. However, due to this erroneous recommendation operators are risking acute dislodgment of the THV due to a short neck of the implanted THV inside the left ventricular outflow, which may cause a future life threatening complication for the patient. The THV is predicted to last about 7-10 years on average until malfunction requiring device replacement. Patients that live longer than this time, and experience valve malfunction, require replacement of the THV valve. The THV may be replaced by open heart surgery, or by implanting another valve within the malfunctioning THV. Due to this recommendation of location for implanting the THV, which Inventor discovered to be erroneous (i.e., implanting the device as close as possible to the aortic annulus) the operators may be eliminating the option of performing a repeated TAVr to implant a new THV inside the malfunctioning THV. This is due to the fact that the original THV is implanted at a very high position relative to the aortic annulus such that the implanted THV takes up the space for replacement valve to be anchored below the aortic annulus level. By eliminating the repeat TAVr procedure these patients are doomed to undergo a complicated open heart surgery that carries a high risk of morbidity and mortality. To address this recommendation which the Inventor discovered to be erroneous, the Inventor recommends to implant the THV at the safest distance from the aortic annulus, for increasing likelihood of (e.g., assuring) a secure anchorage and/or for increasing likelihood of (e.g., assuring) that the distance to the aortic annulus from the current device to allow repeat THV implantation (e.g., may include a third THV within the second THV, etc. . . . ). The THV may be implanted with the distal end of the THV at a distance greater than 0 mm from a plane defining the aortic annulus (e.g., plane defining bottom of cusps of the aortic valve), for at least about 3 mm, or 5 mm, or 7 mm, or 9 mm, or 11 mm or other values greater than 0 mm from the aortic annulus, i.e., from a plane defined as the bottom of the aortic cusps towards the left ventricle. It is noted that existing clinical recommendations are to implant the THV below about 2 mm for some types of THV (e.g., models, manufacturers), while for other THV there is no specific distance. Some physicians implanting THVs try to aim for below about 5 mm.

Inventors also discovered that moving the THV in the partially self-expanded state may lead to damage to the surrounding heart tissue, for example, damage to the conduction system of the heart. The damage may result from scratches and/or scrapes by struts of the scaffold of the partially self-expanded THV (e.g., applied shear forces against the inner tissues of the heart), for example, by ends of the struts, such as point ends and/or joints connecting struts.

At 216, the partially self-expanded portion of the THV is re-compressed into the contracted state, optionally without moving the THV. The whole partially self-expanded portion of the THV may be re-compressed into the contracted state.

The partially self-expanded portion of the THV may be re-compressed into the contracted state when it is determined that the THV is not in the target anatomical location, i.e., when the first anatomical location excludes the target anatomical location for implantation of the THV. When the first anatomical location is different than the target anatomical location, the THV is to be moved to another anatomical location in an attempt to position the THV in the target anatomical location.

As discussed herein, the THV cannot be moved in the partially self-expanded state, and therefore is to be re-compressed into the contracted state, for movement to the other anatomical location while in the contracted state. For example, the first anatomical location within the heart may include sensitive tissues such as the conduction system of the heart. Movement of the portion of the THV that is expanded within the first anatomical location is likely to damage the conduction system.

The re-collapsing of the partially self-expanded portion, and the repositioning of the THV after the re-collapsing to another location may be done for one or more reasons. For example, due to a miss-alignment of an angulation of the THV to an angulation of the valve in which the THV is being deployed (e.g., aortic valve, previously deployed THV). Such miss-alignment may cause a peri-valvular leak. In another example, the repositioning of the THV to another location may be performed to correct the device depth, i.e., a distance between the valve annulus (e.g., defined by a plane at the bottom of the aortic cusps towards the left ventricle) and a distal end of the THV. The device depth is to be according to a requirement (e.g., range), which may be defined by the manufacturer, clinical experimental, best practices, and the like. In yet another example, the repositioning of the THV to another location may be performed in an attempt to avoid or reduce damage to the conduction system from movement of the portion of the THV that is expanded within the first anatomical location.

The re-compression may be performed without moving the THV, for example, by distally displacing the sheath over the partially self-expanded portion of the THV. In another example, the re-compression may be performed by moving the THV, for example, proximally retracting the partially self-expanded portion of the THV into the interior of the sheath. The position of the sheath may be maintained and/or the sheath may be distally displaced while the THV is retracted into the sheath At 218, the THV, which has been re-collapsed from the partially self-expanded state and is in the compressed state, is re-positioned to a second anatomical location within the heart.

The second anatomical location may be selected as the most likely location of the target anatomical location for implantation of the THV, for example, within an annulus of the native aortic valve and/or within a previously implanted artificial heart valve (e.g., THV) that has malfunctioned.

At 220, the THV is fully self-expanded within the target anatomical location. The THV may be fully self-expanded by moving the THV relative to the sheath, for example, by maintaining the position of the THV and proximally retracting the sheath, by maintaining the position of the sheath and distally displacing the THV out of the sheath, and/or combination of the aforementioned by proximally retracting the sheath while distally displacing the THV out of the sheath.

Alternatively, when it is determined that the second anatomical location is not the target anatomical location, the THV may be partially expanded (e.g., to check the location), re-compressed into the contracted state, and moved to another anatomical location in an attempt to position the THV in the target anatomical location, as described herein, for example, by iterating one or more features described with reference to 210-220.

Referring now back to FIG. 3A, THV 302 is shown in the contracted state. No struts of THV 302 are protruding out of a sheath 304 used to deliver THV 302. THV 302 may be moved (e.g., distally, proximally) in the contracted state.

Referring now back to FIG. 3B, THV 302 is shown in a partially self-expanded state 320, where a portion 306 of THV 302 has been self-expanded. Note end regions 308 (two end regions of multiple end regions are marked by arrows) of struts 310 of partially expanded portion 306 of THV 302, which may be sharp. End regions 308 may scrap and/or scratch the interior tissue of the heart (e.g., conduction tissue) when THV 302 is moved (e.g., distally, proximally) while in the partially self-expanded state, as described herein. THV 302 cannot be moved in the partially self-expanded state, as described herein.

Referring now back to FIG. 3C, THV 302 is shown in the fully expanded state 330, optionally implanted in the target anatomical location.

Referring now back to FIG. 4, delivery system 400 may include an expansion controller 402 for controlling expansion and re-collapse of the self-expandable THV 418. Alternatively or additionally, delivery system 400 includes a shaft assembly 410 that includes a shaft 412 for delivery of the THV 418. Shaft assembly 410 may include capsule 414 and a nose element 416 located at a distal end region of shaft 412 in proximity to capsule 414.

The term catheter (of the delivery system) used herein (e.g., with reference to FIG. 6) may refer to shaft assembly 410, optionally with capsule 414 and/or nose element 416.

Expansion controller 402 includes a mechanism 404 for changing an operator applied rate 406 of axial distal displacement or proximal displacement of a capsule 414 housing the self-expandable THV 418 (in the contracted state) for expanding or re-collapse of the self-expandable THV 418, to another rate 408 of axial distal displacement or proximal displacement of the capsule 414 for expanding or re-collapse of the self-expandable THV 418 that is different than the operator applied rate. Mechanism 404 may reduce risk of damage to tissue, by limiting and/or controlling axial movements applied by the operator, for example, controlling speed of axial movements for preventing erroneous fast movements, preventing erroneous movements in a certain direction, and/or preventing erroneous extreme movements.

Expansion controller 402 and/or mechanism 404 may be implemented as, for example, a mechanical mechanism with optional electronic components, including, for example, gears and/or motors and/or an electronic controller.

An operator element 420 may be designed to be operated by the operator for applying operator applied rate 406. For example, operator element 420 may include a lever, wheel, and the like.

An application element 422 may be designed to apply the rate generated mechanism 404 to capsule 414. For example, application element 422 may include a pinch mechanism that grabs shaft 412 and/or a motor that moves shaft 412.

In some embodiments, nose element 416 is shaped as a cone, where the base of the cone is proximally located close to capsule 414, tapering distally to form the cone further away from capsule 414. The length of cone shaped nose element 416 may be less than about 12 mm, or less than 10 mm, or less than about 8 mm, or less than about 6 mm, or other values.

In some embodiments, nose element 416 is shaped as a rounded dome. The round shape may be, for example, approximately a half sphere, and/or a half elliptical sphere and/or less than half. A length of the rounded dome may be is less than about 10 mm, or less than about 8 mm, or less than about 6 mm, or less than about 4 mm, or other values. The radius and/or shape of the rounded dome may substantially match an inner radius and/or shape of the capsule.

In some embodiments, capsule 414 and/or nose element 416 may include an inner channel designed to accommodate a guidewire (e.g., stiff, soft) passes (e.g., guidewire is threaded through). Capsule 414 and/or nose element 416 may be designed such that a distal part of nose element 416 may adjust its pose (e.g., orientation), optionally swiveling freely, relative to capsule 414. For example, nose element 416 may be made of flexible biocompatible material that yields to low pressure, for example, yields in response to movement of the distal end region of the guidewire. In another example, nose element 416 may be placed on a multi-axis hinge that connects between nose element 416 and capsule 416, that enables adjustment to multiple poses. In yet another example, nose release mechanism 430 may release nose element 416 from capsule 414, where a gap between nose element 416 and capsule 414 enables nose element 416 to move to different poses.

Nose element 416 includes an aperture (e.g., fenestration) 416A through which the guidewire passes (e.g., exits out of the nose element). The aperture (e.g., fenestration) 416A of nose element 416 may have an eccentric shape, designed to accommodate the guidewire passing through the aperture for different poses of nose element 416. The eccentric shape may be designed according to the possible orientations of the nose element 416, such that the guidewire passing through does not prevent the different orientations, and/or that the shape of the guidewire is not changed due to pressure from the aperture of the nose element. For example, the eccentric shape is non-circular, such as oval, star shaped, and the like. The design of the nose element and/or capsule to enable changes in pose (e.g., swivel) of the nose element and/or the eccentric shape of the guidewire exit port on the nose element may enable reducing risk of damage to internal tissues of a heart (e.g., conduction system). Optionally, nose release mechanism 430 is designed and/or capable of releasing nose element 416 from capsule 414. Nose release mechanism 430 may be located on the distal end region of capsule 414 and/or proximal end region of nose element 416, for example, serving as a connector that attaches nose element 416 to capsule 414 and releases nose element 416 from capsule 414. Nose release mechanism 430 may be implemented as, for example, mechanically and/or electrically. For example, release mechanism 430 may be implemented as a switch that releases nose element 416 in response to a change of position of the switch, and/or as an electromagnet that attaches nose element 416 to capsule 414 when the electric current is running and releases nose element 416 from capsule 414 when the electric current is off. The nose release mechanism 430 may be operated by the operator from outside the body of the patient, for example, the operator presses a button to activate mechanism 430 to release nose element 416.

The length of nose element 416 may be measured from the bottom of the nose element to the top of the nose element, optionally along a guidewire passing through the nose element. The nose element may be designed to accommodate the guidewire, including a lumen for accommodating the guidewire passing through the nose element from the bottom of the nose element to the top of the nose element.

The shorter length of the nose element and/or the shape of the nose element may reduce risk of damage to tissue, for example, reduced risk of the nose element contacting the inner wall of the left ventricle and/or tissues in proximity to the aortic valve annulus (e.g., conduction system of the heart).

Expansion controller 402 may include a selector 424 designed for selecting between axial distal displacement of capsule 414 or proximal displacement of capsule 414. Selector 424 may be implemented as, for example, a binary switch. Selector 424 may reduce risk of damage to tissue, for example, after the capsule is in the anatomical position, the operator may flip to switch to allow only proximal retraction. Erroneous distal movements of the capsule, which may cause damage to tissues of the heart, is prevented by the switch position.

Expansion controller 402 may changes the operator applied rate 406 to another rate 408 that is pre-set to provide a fast deployment (within a preselected amount of time, optionally to a preselected percentage of a total radius of a fully self-expanded TVH. For example, the deployment is within less than about 1 second, or less than 2 about seconds, or less than about 3 seconds, or less than about 5 seconds, or less than about 10 seconds, or less than about 20 seconds, optionally to about 60%, or about 80% or about 100 of the width of the fully expanded THV, or other values.

Mechanism of 404 of expansion controller 402 may include a stepper mechanism that includes a multiple steps or rotations (or partial rotations) that distally displace capsule 414 or proximally displace capsule 414 a predefined length for each step or rotation (or partial rotation). The predefined length may be the same, or may have different values, for example, initial steps or rotations are large, and later steps are progressively smaller to allow for fine turning. The stepper mechanism may be implemented as, for example, one or more rotary wheels and/or level(s). The length of each step and/or each rotation (or partial rotation) may be, for example, about 8 mm, or about 10 mm, or about 14 mm, or about 22 mm, or about 30 mm, or other values.

Expansion controller 402 may be designed to provide a different ratio between a rate of proximal displacement for covering the capsule and a rate of distal displacement for uncovering the capsule. The rate of proximal displacement may be greater than the rate of proximal displacement for a same movement of the expansion controller (e.g., for a same rotation of the rotary wheel). For example, distal displacement may be slow in order to allow more precise positioning of the capsule for delivery of the THV. Once the THV has been deployed, the capsule may be quickly retracted out of the body.

Referring now back to FIGS. 5A-5E, delivery system 500 includes a nose element 516 (optionally a cone) connected to a capsule 514 housing a THV in the contracted state (not shown). Capsule 514 and nose element 516 may be components of a shaft assembly 510 that further includes a shaft 512. Capsule 514 and nose element 516 include a lumen therethrough designed to accommodate a guidewire 550 for delivery into the body of a subject. Additional details of components of delivery system 500 are described with reference to FIG. 4.

Schematic 560A of FIG. 5A depicts delivery system 500 in a delivery state for passing over guidewire 550 to the target anatomical location within the body of the subject. Nose element 516 is connected to capsule 514. THV is in the contracted state within capsule 514.

Schematic 560B of FIG. 5B depicts an early stage during deployment of the THV. Nose element 516 is separated from capsule 514, by separating a proximal portion 552 of nose element 516 from an interior of capsule 514. An external surface of proximal portion 552 of nose element 516 may be designed to substantially match an interior surface of a distal portion of capsule 514, to enable fitting nose element 516 to capsule 514 and for separating nose element 516 from capsule 514. Nose element 516 is separated from capsule 514, for example, by proximal retraction of capsule 514 (e.g., via shaft 512), by distal displacement of nose element 516, and/or combination of the aforementioned.

Schematic 560C of FIG. 5C depicts release of nose element 516 from capsule 514. Nose element 516 may be released by the nose release mechanism described herein. Nose element 516 may be released after the distal end of the THV has passed through the valve (e.g. aortic valve), as described herein.

Schematic 560D of FIG. 5D depicts further separation of nose element 516 from capsule 514.

Schematic 560E of FIG. 5E depicts release of nose element 516 from capsule 514.

Referring now back to FIG. 6, at 602, deployment of the THV (e.g., self-expandable and/or balloon expandable) in the target anatomical location of the heart of the patient using a catheter of a delivery system has been performed. The deployment of the THV may be performed, for example, as described with reference to FIG. 2, and/or using standard approaches.

Optionally, the THV is a replacement aortic valve, and the target anatomical location is the native aortic valve, optionally the aortic valve annulus.

The THV may be deployment using the catheter that rides over the stiff guidewire. The stiff guidewire may be used for inserting the THV into the target anatomical position via a stenotic (e.g., severely stenotic) aortic valve. The soft guidewire may be passable through the stenotic aortic valve, for example, the soft guidewire may be too flexible, falling into one of the cusps rather than passing through the aperture of the stenotic aortic valve.

Optionally, after the deployment of the THV, a distal region of the stiff guidewire is located in the left ventricle. The distal region of the stiff guidewire may serve as an anchor for the portion of the stiff guidewire passing through the native aortic valve which is used for passing the catheter housing the THV.

At 604, the catheter may be repositioned prior to exchanging the stiff guidewire, for example, for reducing risk of damage to heart tissue during the exchange of the stiff guidewire.

Optionally, the catheter is retracted proximally to the deployed THV (i.e., antegrade direction), until a distal end region of the catheter is located proximally to the deployed self-expanding THV. The catheter may not be located within the deployed THV, but just above the deployed THV.

Alternatively or additionally, a distal end region of the catheter is distally displaced into the left ventricle by crossing the deployed THV.

Alternatively or additionally, the distal end region of the catheter is not repositioned prior to the exchange. The distal end region of the catheter may be left in its current position, for example, antegrade above the deployed THV, within the deployed THV, or retrograde past the deployed THV and within the left ventricle.

Alternatively or additionally, the distal region of the catheter and the distal region of the stiff guidewire are not moved to a substantially center of the deployed THV. Such movement of the distal region of the catheter and the distal region of the stiff guidewire to the approximate center of the deployed THV may be required using standard approaches, which may lead to damage of tissues of the heart by the stiff guidewire, as described herein.

At 606, the stiff guidewire over which the catheter is riding, and which has been used to deploy the THV, is exchanged to the soft guidewire.

Optionally, the stiff guidewire is exchanged without necessarily positioning the distal region of the catheter and a distal region of the stiff guidewire in a substantially center of the deployed THV.

Alternatively or additionally, when the catheter has been retracted proximally to the deployed THV the exchange may be performed by retracting the stiff guidewire out of the body, and inserting a distal end region of the soft guidewire though the deployed THV into the left ventricle. The soft guidewire is able to pass through the deployed THV since there is no stenosis, the opening of the deployed self-expanding THV is large enough to accommodate the soft guidewire without causing the soft guidewire to bend to the side (as would occur in trying to pass the soft guidewire through a stenotic native valve, which may be a reason for using the stiff guidewire, as discussed above).

Alternatively or additionally, when the distal end region of the catheter has been positioned into the left ventricle, the exchange may be performed by retracting the stiff guidewire out of the body and inserting the distal end region of the soft guidewire though the distal end region of the catheter into the left ventricle. The catheter acts as the guide for positioning the soft guidewire within the left ventricle. Using the soft guidewire avoids or reduces risk of damage to the left ventricle, since the soft guidewire bends in response to being pushed against tissues of the left ventricle, rather than puncturing and/or damaging the tissues as may likely occur by using the stiff guidewire.

The difference between the stiff guidewire and the soft guidewire may be, for example, based on a flexural modulus (i.e., bending modulus). The stiff guidewire has a value of the flexural modulus above a threshold, while the soft guidewire may have the value below the threshold. The value of the flexural modulus of the stiff guidewire may be much larger than the value of the flexural modulus of the soft guidewire. The stiff guidewire may be capable of crossing a stenotic native aortic valve with small opening area (which is to be replaced with the THV) without being bent to the sides (e.g., cusps), while the soft guidewire bends in response to an attempt to cross the stenotic native aortic valve (e.g., bends to the side, such as the cusps), without crossing the stenotic native aortic valve. The stiff guidewire may be capable of damaging tissue of the interior of the heart (e.g., left ventricle) by distal displacement into the tissue, for example, the end of the stiff guidewire may puncture the tissues leading to damage to the conduction tissue and/or cardiac tamponade. In contrast, the soft guidewire may bend in response to distal displacement into the tissue, which does not cause the damage to the tissue that would be caused by applying the same pushing force to the stiff guidewire.

At 608, the catheter of the delivery system may be extracted from the body of the patient over the soft guidewire.

The catheter of the delivery system may be extracted while retaining the distal region of the soft guidewire in the left ventricle. The distal region of the soft guidewire may be located and/or placed in the left ventricle prior and/or during the exchange.

At 610, the soft guidewire may be extracted out of the body of the patient after extracting the delivery system out of the body of the patient. The access point may be closed.

It is expected that during the life of a patent maturing from this application many relevant artificial heart valves will be developed and the scope of the term artificial heart valve is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a patient, comprising:
    delivering a self-expandable transcatheter heart valve (THV) over a guidewire in a contracted state and within a sheath to a first anatomical location within a heart of the patient,
    wherein the THV includes inflow struts with sharp end regions;
    moving the THV relative to the sheath for partially self-expanding a portion of the THV within the first anatomical location, wherein a portion of the THV in the sheath remains in the contracted state and the THV is partially self-expanded,
    wherein a distal end of the THV is positioned 3-10 millimeters (mm) from a plane defined as a bottom of cusps of an aortic valve towards a left ventricle;
    wherein the portion of the THV that is partially self-expanded includes any of the inflow struts of the THV protruding out of the sheath;
    refraining from moving the partially self-expanded THV with any of the inflow struts protruding out of the sheath, relative to an aortic annulus of the heart;
    re-collapsing the partially self-expanded portion;
    repositioning the distal end of the THV after the re-collapsing to a second anatomical location within the heart 3-10 mm from the plane; and
    deploying the THV such that the distal end of the THV is 3-10 mm from the plane.

2. The method of claim 1, wherein refraining from moving the partially self-expanded portion of the THV within the heart is selected from a group comprising: not proximally displacing, not distally displacing, and not rotating.

3. The method of claim 1, wherein the first anatomical location excludes a target anatomical location for implantation of the THV.

4. The method of claim 1, wherein the first anatomical location within the heart is in proximity to the bundle of HIS and/or AV node of a conduction system of the heart, and movement of the portion of the THV that is expanded within the first anatomical location damages the conduction system causing a conduction block, and wherein the re-collapsing the partially self-expanded portion, and the repositioning the THV after the re-collapsing, are for avoiding or reducing damage to the conduction system from movement of the portion of the THV that is expanded within the first anatomical location.

5. The method of claim 1, wherein the portion of the THV is partially self-expanded when a distal end of the THV is larger by at least about 3 millimeters above a diameter of the THV in the contracted state.

6. The method of claim 1, further comprising starting release of a nose element of the THV after a distal end of a nose element of a delivery system of the THV passed through the aortic annulus.

7. The method of claim 1, further comprising inflating a balloon within a native valve in which the self-expandable THV is to deployed prior to passing the self-expandable THV over the guidewire.

8. The method of claim 7, further comprising prior to inflating the balloon, checking whether a second catheter is positioned in proximity to the aortic annulus, and not inflating the balloon when the second catheter is positioned in proximity to the aortic annulus, and inflating the balloon when the second catheter is not positioned in proximity to the aortic annulus.

9. The method of claim 8, wherein the second catheter is positioned in proximity to the aortic annulus comprises the second catheter is positioned within about 4 centimeters (cm) from the aortic annulus.

10. The method of claim 8, wherein the second catheter is positioned in proximity to the aortic annulus comprises the second catheter is positioned between aortic valve cusps of the aortic valve.

11. The method of claim 8, further comprising prior to the inflating the balloon, moving the second catheter from tissues being compressed by expansion of the balloon during inflation.

12. The method of claim 8, further comprising prior to inflating the balloon, moving the second catheter to a left coronary cusp.

13. The method of claim 7, further comprising inflating the balloon while maintaining a constant location of the balloon during inflation from an initial position of the balloon at the beginning of inflation.

14. The method of claim 1, further comprising prior to delivering the THV over the guidewire, inserting the guidewire used for delivering the THV into the left ventricle.

15. The method of claim 14, further comprising during the insertion of the guidewire, creating curves of the guidewire each of a local radius of at least about 0.6 millimeters (mm), wherein no curve of the guidewire is less than about 0.6 mm.

16. The method of claim 1, further comprising maintaining a substantially constant location of a distal end of the guidewire while at least one of the THV and a balloon are being delivered over the guidewire or removed over the guidewire.

17. The method of claim 16, wherein the distal end of the guidewire is maintained in the substantially constant location within the left ventricle.

18. The method of claim 1, wherein the patient suffers from a non-healthy aortic heart valve, and the patient is treated using a transcatheter aortic valve replacement (TAVR) procedure for replacing the non-healthy aortic heart valve with a transcatheter aortic valve.

19. The method of claim 18, wherein the patient suffers from aortic stenosis.

20. The method of claim 1, further comprising moving the THV relative to the sheath for full self-expansion of the THV within the second anatomical location within the heart.

21. The method of claim 1, wherein a nose element of a delivery system for delivering the THV is shaped as a rounded dome.

22. The method of claim 1, wherein a nose element of the a delivery system for delivering the THV is shaped as an swiveling dome with an eccentrically shaped aperture through which the guidewire passes, designed to accommodate the guidewire for different poses of the nose element.

23. The method of claim 1, wherein a delivery system for delivering the THV includes a nose release mechanism configured for quick release of the nose element after passing through the plane.

24. The method of claim 1, wherein a nose element of a delivery system for delivering the THV has a length of less than about 6 mm.

25. The method of claim 1, wherein a nose element of a delivery system for delivering the THV is designed such that a distal port of the nose element is capable of adjusting its posture by swiveling freely relative to a capsule.

26. A method of treating a patient, comprising:
delivering a self-expandable transcatheter heart valve (THV) over a guidewire and within a sheath to a first anatomical location within a heart of the patient,
wherein the THV includes inflow struts with sharp end regions;
moving the THV relative to the sheath for partially self-expanding a portion of the THV within the first anatomical location, wherein a portion of the THV in the sheath remains in a contracted state,
wherein a distal end of the THV is positioned 3-10 millimeters (mm) from a plane defined as a bottom of cusps of an aortic valve towards a left ventricle;
wherein the portion of the THV that is partially self-expanded includes any of the inflow struts of the THV protruding out of the sheath,
refraining from moving the partially self-expanded THV with any of the inflow struts protruding out of the sheath, relative to an aortic annulus of the heart;
completing the withdrawal of the sheath for expanding the portion of the THV in the contracted state while refraining from moving the THV, relative to an aortic annulus of the heart; and
deploying the THV such that the distal end of the THV is 3-10 mm from the plane.

27. A method of treating a patient, comprising:
delivering a self-expandable transcatheter heart valve (THV) over a guidewire in a contracted state and within a sheath to a first anatomical location within a heart of the patient,
deploying the THV such that the distal end of the THV is 3-10 mm from the plane;
moving the THV relative to the sheath for partially self-expanding a portion of the THV within the first anatomical location, wherein a portion of the THV in the sheath remains in the contracted state,
wherein a distal end of the THV is positioned 3-10 millimeters (mm) from a plane defined as a bottom of cusps of an aortic valve towards a left ventricle;
wherein the portion of the THV that is partially self-expanded includes any of the inflow struts of the THV protruding out of the sheath,
refraining from moving the partially self-expanded THV with any of the inflow struts protruding out of the sheath, relative to an aortic annulus of the heart;
re-compressing the expanded portion of the THV by moving the sheath over the expanded portion of the THV while refraining from moving the THV relative to an aortic annulus of the heart and positioning the compressed THV to a second anatomical location 3-10 mm from the plane; and
deploying the THV such that the distal end of the THV is 3-10 mm from the plane.

28. A method of treating a patient, comprising:
delivering a self-expandable transcatheter heart valve (THV) over a guidewire in a contracted state and within a sheath to a first anatomical location within a heart of the patient,
wherein the THV includes inflow struts with sharp end regions;
moving the THV relative to the sheath for partially self-expanding a portion of the THV within the first anatomical location, wherein a portion of the THV in the sheath remains in the contracted state and the THV is partially self-expanded,
wherein a distal end of the THV is positioned 3-10 millimeters (mm) from a plane defined as a bottom of cusps of an aortic valve towards a left ventricle;
wherein the portion of the THV that is partially self-expanded includes any of the inflow struts of the THV protruding out of the sheath,
refraining from moving the partially self-expanded THV with any of the inflow struts protruding out of the sheath, relative to an aortic annulus of the heart;
without moving the partially self-expanded portion of the THV within the heart, distally displacing the sheath relative to the partially self-expanded portion of the THV for re-collapsing the partially self-expanded portion of the THV into the contracted state;

after the re-collapsing of the partially self-expanded portion, repositioning the THV to a second anatomical location within the heart 3-10 mm from the plane;

moving the THV relative to the sheath for full self-expansion of the THV within the second anatomical location; and deploying the THV such that the distal end of the THV is 3-10 mm from the plane.

29. The method of claim 28, wherein the second anatomical location is within a previously implanted artificial heart valve that has malfunctioned.

* * * * *